United States Patent
Lizardi et al.

(10) Patent No.: US 8,617,176 B2
(45) Date of Patent: Dec. 31, 2013

(54) CROSS PINNING GUIDE DEVICES AND METHODS

(75) Inventors: Jose E. Lizardi, Franklin, MA (US);
Peter Reynaert, Boortmeerbeek (BE);
Stephen J. Orphanos, Bridgewater, MA (US); David Spenciner, Attleboro, MA (US)

(73) Assignee: DePuy Mitek, LLC, Raynham, MA (US)

( * ) Notice: Subject to any disclaimer, the term of this patent is extended or adjusted under 35 U.S.C. 154(b) by 167 days.

(21) Appl. No.: 13/216,947

(22) Filed: Aug. 24, 2011

(65) Prior Publication Data
US 2013/0053959 A1    Feb. 28, 2013

(51) Int. Cl.
*A61F 2/08* (2006.01)
*A61F 2/00* (2006.01)
*A61B 17/58* (2006.01)

(52) U.S. Cl.
USPC ......... 606/98; 623/13.12; 623/13.14; 606/87; 606/88; 606/96

(58) Field of Classification Search
USPC ........ 623/13.11–13.14; 606/86 R–90, 96–98, 606/102, 104, 54, 56, 62
See application file for complete search history.

(56) References Cited

U.S. PATENT DOCUMENTS

| | | | |
|---|---|---|---|
| 2,112,337 A | 3/1938 | Gillespie |
| 3,973,277 A | 8/1976 | Semple et al. |
| 4,013,071 A | 3/1977 | Rosenberg |
| 4,022,191 A | 5/1977 | Jamshidi |
| 4,257,411 A | 3/1981 | Cho |
| 4,431,200 A | 2/1984 | Sugimura |
| 4,462,395 A | 7/1984 | Johnson |
| 4,535,768 A | 8/1985 | Hourahane et al. |
| 4,541,424 A | 9/1985 | Grosse et al. |
| 4,590,928 A | 5/1986 | Hunt et al. |
| 4,672,957 A | 6/1987 | Hourahane |
| 4,744,353 A | 5/1988 | McFarland |
| 4,760,843 A | 8/1988 | Fischer et al. |
| 4,787,377 A | 11/1988 | Laboureau |
| 4,792,336 A | 12/1988 | Hlavacek et al. |
| 4,809,694 A | 3/1989 | Ferrara |

(Continued)

FOREIGN PATENT DOCUMENTS

DE    19510372 C1    7/1996
EP    0933064 A2    8/1999

(Continued)

OTHER PUBLICATIONS

European Search Report for Application No. 12181791.0, issued Nov. 26, 2012. (6 pages).

*Primary Examiner* — David Isabella
*Assistant Examiner* — Yashita Sharma

(57) ABSTRACT

Methods and devices are provided for implanting a cross-pin through a bone tunnel, such as in an arthroscopic surgical procedure. In general, the methods and devices allow a cross-pin hole to be formed in a medial side of a knee bone such that it intersects a bone tunnel formed in the knee bone. In one embodiment, a cross-pinning guide device is provided that can be configured to angularly position the cross-pin hole relative to the bone tunnel to allow the cross-pin hole to intersect the bone tunnel without passing through another side, e.g., a lateral side, of the knee bone. The knee bone can be a femur or a tibia such that the cross-pin hole and the bone tunnel can each be entirely formed in the femur or in the tibia.

10 Claims, 17 Drawing Sheets

(56) References Cited

U.S. PATENT DOCUMENTS

| | | |
|---|---|---|
| 4,848,327 A | 7/1989 | Perdue |
| 4,858,603 A | 8/1989 | Clemow et al. |
| 4,898,156 A | 2/1990 | Gatturna et al. |
| 4,899,743 A | 2/1990 | Nicholson et al. |
| 4,901,711 A | 2/1990 | Goble et al. |
| 4,911,153 A | 3/1990 | Border |
| 4,944,742 A | 7/1990 | Clemow et al. |
| 4,950,270 A | 8/1990 | Bowman et al. |
| 4,968,315 A | 11/1990 | Gatturna |
| 4,985,032 A | 1/1991 | Goble |
| 4,986,833 A | 1/1991 | Worland |
| 5,004,474 A | 4/1991 | Fronk et al. |
| 5,013,318 A | 5/1991 | Spranza, III |
| 5,031,634 A | 7/1991 | Simon |
| 5,053,042 A | 10/1991 | Bidwell |
| 5,067,962 A | 11/1991 | Campbell et al. |
| 5,080,673 A | 1/1992 | Burkhead et al. |
| 5,098,435 A | 3/1992 | Stednitz et al. |
| 5,100,387 A | 3/1992 | Ng |
| 5,108,446 A | 4/1992 | Wagner et al. |
| 5,116,372 A | 5/1992 | Laboureau |
| 5,120,318 A | 6/1992 | Nallapareddy |
| 5,139,520 A | 8/1992 | Rosenberg |
| 5,147,362 A | 9/1992 | Goble |
| 5,152,764 A | 10/1992 | Goble et al. |
| 5,154,720 A | 10/1992 | Trott et al. |
| 5,163,940 A | 11/1992 | Bourque |
| 5,169,400 A | 12/1992 | Muhling et al. |
| 5,192,322 A | 3/1993 | Koch et al. |
| 5,201,742 A | 4/1993 | Hasson |
| 5,209,753 A | 5/1993 | Biedermann et al. |
| 5,234,434 A | 8/1993 | Goble et al. |
| 5,235,987 A | 8/1993 | Wolfe |
| 5,257,996 A | 11/1993 | McGuire |
| 5,266,075 A | 11/1993 | Clark et al. |
| 5,298,012 A | 3/1994 | Handlos |
| 5,306,278 A | 4/1994 | Dahl et al. |
| 5,312,409 A | 5/1994 | McLaughlin et al. |
| 5,314,429 A | 5/1994 | Goble |
| 5,314,487 A | 5/1994 | Schryver et al. |
| 5,316,014 A | 5/1994 | Livingston |
| 5,318,578 A | 6/1994 | Hasson |
| 5,320,111 A | 6/1994 | Livingston |
| 5,320,626 A | 6/1994 | Schmieding |
| 5,324,295 A | 6/1994 | Shapiro |
| 5,330,468 A | 7/1994 | Burkhart |
| 5,350,380 A | 9/1994 | Goble et al. |
| 5,354,300 A | 10/1994 | Goble et al. |
| 5,356,413 A | 10/1994 | Martins et al. |
| 5,356,435 A | 10/1994 | Thein |
| 5,364,400 A | 11/1994 | Rego, Jr. et al. |
| 5,372,599 A | 12/1994 | Martins |
| 5,376,119 A | 12/1994 | Zimmermann et al. |
| 5,393,302 A | 2/1995 | Clark et al. |
| 5,397,356 A | 3/1995 | Goble et al. |
| 5,431,651 A | 7/1995 | Goble |
| 5,470,334 A | 11/1995 | Ross et al. |
| 5,494,039 A | 2/1996 | Onik et al. |
| 5,522,817 A | 6/1996 | Sander et al. |
| 5,530,380 A | 6/1996 | Kondoh |
| 5,556,411 A | 9/1996 | Taoda et al. |
| 5,562,664 A | 10/1996 | Durlacher et al. |
| 5,562,671 A | 10/1996 | Goble et al. |
| 5,570,706 A | 11/1996 | Howell |
| 5,601,550 A | 2/1997 | Esser |
| 5,601,562 A | 2/1997 | Wolf et al. |
| 5,603,716 A | 2/1997 | Morgan et al. |
| 5,647,373 A | 7/1997 | Paltieli et al. |
| 5,669,885 A | 9/1997 | Smith |
| 5,672,158 A | 9/1997 | Okada et al. |
| 5,674,224 A | 10/1997 | Howell et al. |
| 5,681,320 A | 10/1997 | McGuire |
| 5,688,284 A | 11/1997 | Chervitz et al. |
| 5,697,933 A | 12/1997 | Gundlapalli et al. |
| 5,702,447 A | 12/1997 | Walch et al. |
| RE36,020 E | 12/1998 | Moore et al. |
| 5,849,013 A | 12/1998 | Whittaker et al. |
| 5,868,673 A | 2/1999 | Vesely |
| 5,891,150 A | 4/1999 | Chan |
| 5,895,425 A | 4/1999 | Grafton et al. |
| 5,911,707 A | 6/1999 | Wolvek et al. |
| 5,916,175 A | 6/1999 | Bauer et al. |
| 5,918,604 A | 7/1999 | Whelan |
| 5,919,193 A | 7/1999 | Slavitt |
| 5,931,840 A | 8/1999 | Goble et al. |
| 5,941,889 A | 8/1999 | Cermak |
| 5,954,670 A | 9/1999 | Baker |
| 5,957,947 A | 9/1999 | Wattiez et al. |
| 5,984,930 A | 11/1999 | Maciunas et al. |
| 6,022,356 A | 2/2000 | Noyes et al. |
| 6,027,506 A | 2/2000 | Faccioli et al. |
| 6,030,364 A | 2/2000 | Durgin et al. |
| D422,706 S | 4/2000 | Bucholz et al. |
| 6,048,321 A | 4/2000 | McPherson et al. |
| 6,056,752 A | 5/2000 | Roger |
| 6,066,173 A | 5/2000 | McKernan et al. |
| 6,096,060 A | 8/2000 | Fitts et al. |
| 6,123,710 A | 9/2000 | Pinczewski et al. |
| 6,132,433 A | 10/2000 | Whelan |
| 6,187,011 B1 | 2/2001 | Torrie |
| 6,195,577 B1 | 2/2001 | Truwit et al. |
| 6,203,499 B1 | 3/2001 | Imling |
| 6,216,029 B1 | 4/2001 | Paltieli et al. |
| 6,231,565 B1 | 5/2001 | Tovey et al. |
| 6,231,585 B1 | 5/2001 | Takahashi et al. |
| 6,236,875 B1 | 5/2001 | Bucholz et al. |
| 6,245,028 B1 | 6/2001 | Furst et al. |
| 6,254,606 B1 | 7/2001 | Carney et al. |
| 6,280,472 B1 | 8/2001 | Boucher et al. |
| 6,283,942 B1 | 9/2001 | Staehlin et al. |
| 6,306,138 B1 | 10/2001 | Clark et al. |
| 6,325,804 B1 | 12/2001 | Wenstrom, Jr. et al. |
| 6,342,056 B1 | 1/2002 | Mac-Thiong et al. |
| 6,361,499 B1 | 3/2002 | Bates et al. |
| 6,379,307 B1 | 4/2002 | Filly et al. |
| 6,379,384 B1 | 4/2002 | McKernan et al. |
| 6,400,979 B1 | 6/2002 | Stoianovici et al. |
| 6,436,100 B1 | 8/2002 | Berger |
| 6,436,119 B1 | 8/2002 | Erb et al. |
| 6,443,960 B1 | 9/2002 | Brabrand et al. |
| 6,445,943 B1 | 9/2002 | Ferre et al. |
| 6,450,812 B1 | 9/2002 | Laster et al. |
| 6,468,226 B1 | 10/2002 | McIntyre, IV |
| 6,475,152 B1 | 11/2002 | Kelly, Jr. et al. |
| 6,490,467 B1 | 12/2002 | Bucholz et al. |
| 6,501,981 B1 | 12/2002 | Schweikard et al. |
| 6,517,546 B2 | 2/2003 | Whittaker et al. |
| 6,529,765 B1 | 3/2003 | Franck et al. |
| 6,535,756 B1 | 3/2003 | Simon et al. |
| 6,539,121 B1 | 3/2003 | Haskell et al. |
| 6,546,279 B1 | 4/2003 | Bova et al. |
| 6,547,782 B1 | 4/2003 | Taylor |
| 6,547,795 B2 | 4/2003 | Schneiderman |
| 6,632,245 B2 | 10/2003 | Kim |
| 6,665,554 B1 | 12/2003 | Charles et al. |
| 6,669,698 B1 | 12/2003 | Tromanhauser et al. |
| 6,687,531 B1 | 2/2004 | Ferre et al. |
| 6,723,106 B1 | 4/2004 | Charles et al. |
| 6,723,125 B2 | 4/2004 | Heckele et al. |
| 6,731,966 B1 | 5/2004 | Spigelman et al. |
| 6,770,027 B2 | 8/2004 | Banik et al. |
| 6,770,076 B2 | 8/2004 | Foerster |
| 6,782,288 B2 | 8/2004 | Truwit |
| 6,783,524 B2 | 8/2004 | Anderson |
| 6,785,572 B2 | 8/2004 | Yanof et al. |
| 6,808,528 B2 | 10/2004 | Justin |
| 6,869,434 B2 | 3/2005 | Choi |
| 6,902,526 B2 | 6/2005 | Katzman |
| 6,958,067 B2 | 10/2005 | Whittaker et al. |
| 7,014,461 B2 | 3/2006 | Weinstein |
| 7,021,173 B2 | 4/2006 | Stoianovici et al. |
| 7,076,106 B2 | 7/2006 | Haskell et al. |
| 7,094,200 B2 | 8/2006 | Katzman |
| 7,195,642 B2 | 3/2007 | McKernan et al. |

(56) References Cited

U.S. PATENT DOCUMENTS

| | | |
|---|---|---|
| 7,491,206 B2 | 2/2009 | Whittaker et al. |
| 7,494,490 B2 | 2/2009 | Justin |
| 7,594,917 B2 | 9/2009 | Whittaker et al. |
| 7,655,011 B2 | 2/2010 | Whittaker et al. |
| 7,674,290 B2 | 3/2010 | McKernan et al. |
| 2001/0018619 A1 | 8/2001 | Enzerink et al. |
| 2001/0044659 A1 | 11/2001 | Laboureau et al. |
| 2002/0165611 A1 | 11/2002 | Enzerink et al. |
| 2002/0173849 A1 | 11/2002 | McKernan et al. |
| 2003/0100814 A1 | 5/2003 | Kindlein |
| 2003/0220651 A1 | 11/2003 | Pusnik et al. |
| 2004/0049195 A1 | 3/2004 | Singhatat et al. |
| 2004/0082959 A1 | 4/2004 | Hayes et al. |
| 2004/0210232 A1 | 10/2004 | Patel et al. |
| 2005/0143831 A1 | 6/2005 | Justin et al. |
| 2005/0177171 A1 | 8/2005 | Wetzler et al. |
| 2006/0069394 A1 | 3/2006 | Weiler et al. |
| 2006/0240379 A1 | 10/2006 | Weinstein |
| 2006/0271059 A1 | 11/2006 | Reay-Young et al. |
| 2007/0162122 A1 | 7/2007 | Whittaker |
| 2007/0162123 A1 | 7/2007 | Whittaker et al. |
| 2008/0103506 A1 | 5/2008 | Volpi et al. |
| 2009/0093880 A1 | 4/2009 | Justin |
| 2009/0306675 A1 | 12/2009 | Wong et al. |
| 2010/0030222 A1 | 2/2010 | Whittaker et al. |
| 2010/0057142 A1 | 3/2010 | Whittaker et al. |
| 2010/0121339 A1 | 5/2010 | Whittaker et al. |
| 2010/0121448 A1 | 5/2010 | McKernan et al. |
| 2010/0160925 A1 | 6/2010 | Heilala et al. |

FOREIGN PATENT DOCUMENTS

| | | |
|---|---|---|
| EP | 1449484 A1 | 8/2004 |
| FR | 2552655 A1 | 4/1985 |
| FR | 2560764 A1 | 9/1985 |
| FR | 2598311 A1 | 11/1987 |
| FR | 2716364 A1 | 8/1995 |
| FR | 2880292 A1 | 7/2006 |
| JP | 2-057247 A | 2/1990 |
| JP | 4338470 A | 11/1992 |
| JP | 5123336 A | 5/1993 |
| JP | 9-075354 A | 3/1997 |
| JP | 9140721 A | 6/1997 |
| JP | 2000210311 | 8/2000 |
| JP | 2001507977 | 6/2001 |
| WO | WO-94/15556 A1 | 7/1994 |
| WO | WO-98/30162 A1 | 7/1998 |
| WO | WO-98/35621 A1 | 8/1998 |
| WO | WO-9915095 A1 | 4/1999 |
| WO | WO-99/52453 A2 | 10/1999 |
| WO | WO-02/071958 A1 | 9/2002 |
| WO | WO-03/037163 A2 | 5/2003 |
| WO | WO-2006125009 A2 | 11/2006 |

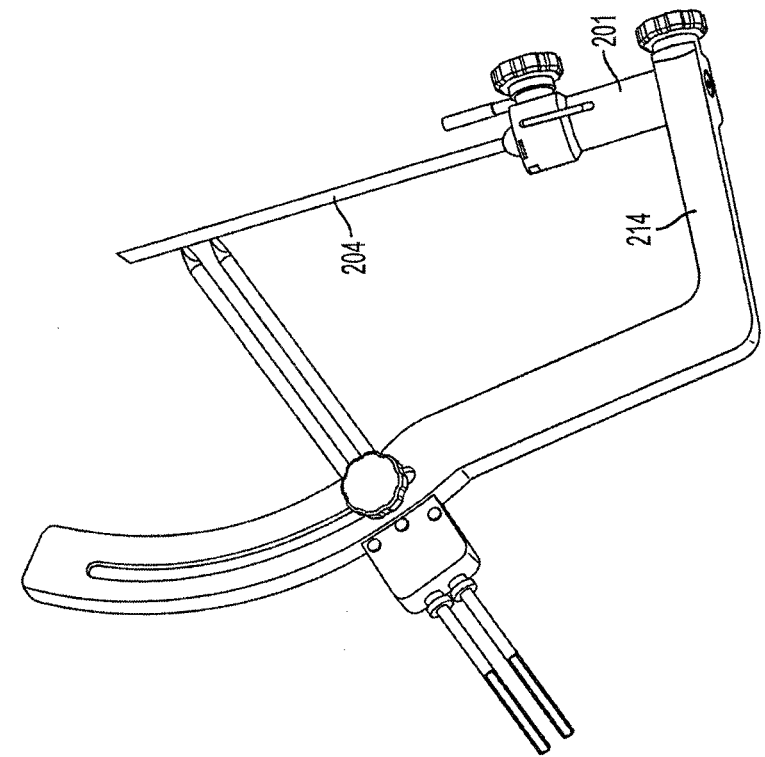
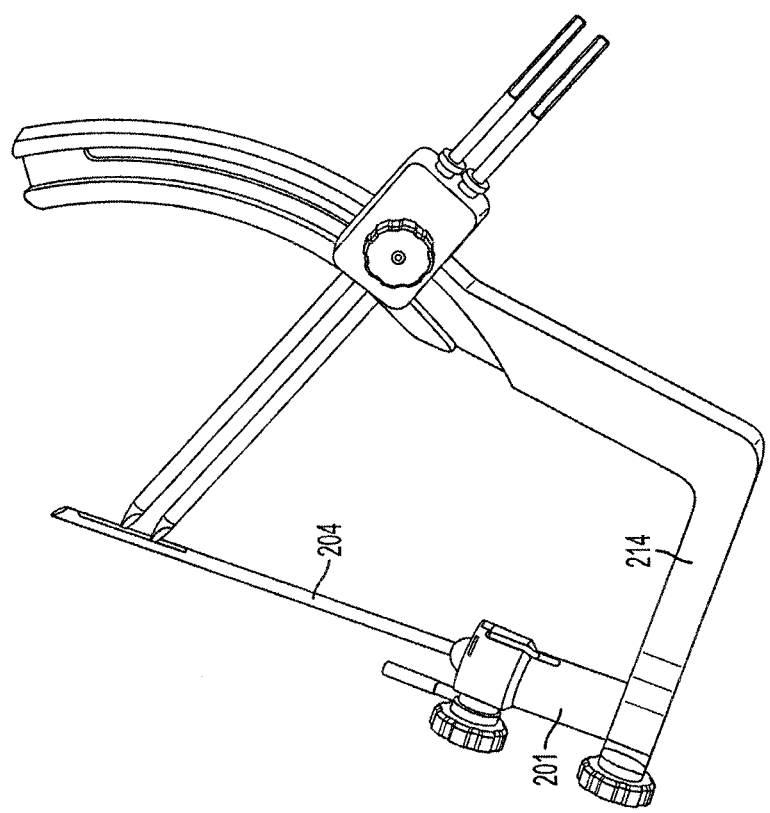
FIG. 4
FIG. 3

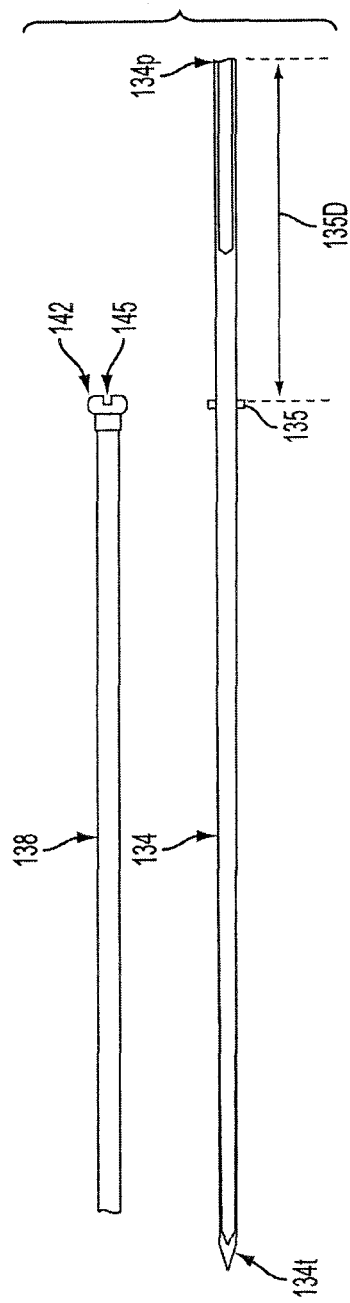
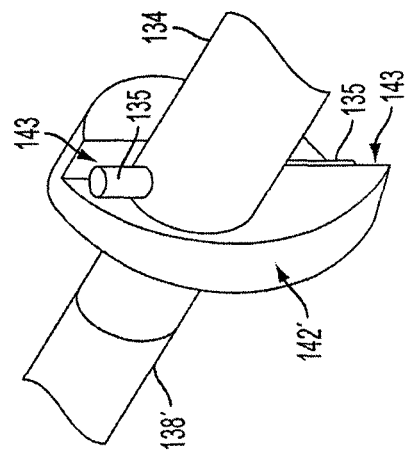
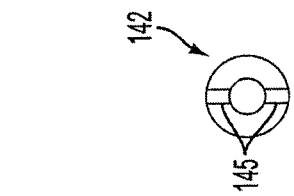
FIG. 7
FIG. 9
FIG. 8

CROSS PINNING GUIDE DEVICES AND METHODS

FIELD OF THE INVENTION

The present invention relates generally to orthopedic methods and devices, and in particular to methods and devices for use in arthroscopic repair of soft tissue injuries.

BACKGROUND OF THE INVENTION

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves forming aligned femoral and tibial tunnels in a human knee, such as in repairing a damaged anterior cruciate ligament ("ACL"). A bone block or anchor with a ligament graft attached thereto is passed through the tunnels to a blind end of the femoral tunnel where the block or anchor is fixed in place. The ligament extends out of the tibial tunnel, and the end is attached to the tibia cortex by staples or the like. Alternatively, the end of the ligament may be fixed in the tibial tunnel by an anchor or by an interference screw. Various types of ligament and/or suture anchors for attaching soft tissue to bone are well known in the art.

One method for anchoring bone blocks in bone tunnels is through cross-pinning, in which a cross pin such as a pin, screw, or rod is inserted into the bone, transversely to the bone tunnel, so as to intersect the ligament graft and/or the bone block, to "cross-pin" the graft in the bone tunnel. The cross pin is generally placed in a pre-drilled tunnel in the bone that is prepared using a drill guide.

In addition, considerations for cross-pinning graft ligaments in the tibia differ from considerations for cross-pinning of graft ligaments in the femur. These considerations include differences in anatomical geometry, bone quality, and other considerations. These different requirements generally result in the development and application of different cross-pinning guides for femoral and tibial cross-pinning, adding complexity and expense to the performance of tissue reattachment surgeries such as ACL replacement surgeries.

Accordingly, there is a need for improved methods and devices for repairing ligaments and for positioning and forming bone tunnels.

SUMMARY OF THE INVENTION

In one embodiment, a cross pinning guide device is provided that includes a frame having a guide rod and a proximal-distal arc spaced a distance apart from the guide rod, a guide block slidably mounted on the proximal-distal arc and having at least one bore formed therethrough that is configured to receive a first surgical instrument, e.g., a cross pin, a drill sleeve, etc., and a medial-lateral arc having a first end with an engagement mechanism configured to detachably mate the medial-lateral arc to the guide block, and a second end having at least one bore formed therethrough that is configured to receive a second surgical instrument, e.g., a needle, a tunnel guide, etc.

The medial-lateral arc and the guide block, and the respective bore(s) formed therethrough, can have a variety of orientations relative to one another when the medial-lateral arc and the guide block are mated together. For example, with the medial-lateral arc mated to the guide block, the medial-lateral arc can be positioned in a plane that is substantially perpendicular to a plane containing the proximal-distal arc. For another example, with the medial-lateral arc mated to the guide block, the at least one bore formed through the guide block can be coaxial with the at least one bore formed through the second end of the medial-lateral arc.

The at least one bore formed through the guide block and the at least one bore formed through the medial-lateral arc can have a variety of configurations. In one embodiment, the at least one bore formed through the guide block can include first and second bores, and the at least one bore formed through the second end of the medial-lateral arc can include third and fourth bores. With the medial-lateral arc mated to the guide block, the first bore can be coaxial with the third bore, and the second bore can be coaxial with the fourth bore. In another embodiment, the at least one bore formed through the guide block can include first and second bores, and the at least one bore formed through the second end of the medial-lateral arc can include a single bore. With the medial-lateral arc mated to the guide block, a longitudinal axis of the single bore can be parallel to and positioned between longitudinal axes of the first and second bores.

The engagement mechanism of the medial-lateral arc can be matable with the guide block in a first orientation relative to the guide block and in a second orientation relative to the guide block that differs from the first orientation. With the medial-lateral arc mated to the guide block, the medial-lateral arc in the first orientation can be seated in a first hole formed in the guide block, and in the second orientation can be seated in a second hole formed in the guide block.

In other aspects, with the guide block at any slidable position along the proximal-distal arc, a longitudinal axis of the at least one bore formed through the guide block can extend through an opening formed in a distal portion of the guide rod. With the medial-lateral arc mated to the guide block, a longitudinal axis of the at least one bore formed through the second end of the medial-lateral arc can extend through the opening formed in the distal portion of the guide rod.

The frame can also have a variety of configurations. In an exemplary embodiment, the proximal-distal arc can extend in a direction substantially parallel to a direction of the guide rod.

In another aspect, a method for implanting a cross-pin through a bone tunnel is provided that includes positioning a guide block of a cross pinning guide device on a medial side of a knee bone, e.g., a femur or a tibia, and positioning a needle guide of the cross pinning guide device on a lateral side of the knee bone, and adjusting a trajectory of a bore extending through the guide block based on an insertion depth of a needle inserted through a bore in the needle guide and into tissue on the lateral side of the knee bone.

The trajectory of the bore extending through the guide block can be adjusted in a variety of ways. For example, adjusting the trajectory of the bore extending through the guide block can include rotating the cross pinning guide device relative to the knee bone about a longitudinal axis of a bone tunnel formed in the knee bone. For another example, the guide block can be mated to a proximal-distal frame of the cross pinning guide device, and adjusting the trajectory of the bore extending through the guide block can include sliding the guide block along the proximal-distal frame. For yet another example, the trajectory can be adjusted based on a first distance between a mark on the needle positioned lateral of the bore in the needle guide and a lateral face of the needle guide. The first distance can be equal to or less than a second distance between a bone surface on the lateral side of the knee bone and a lateral terminal end of a medial-lateral bone tunnel formed in the knee bone.

Prior to adjusting the trajectory of the bore extending through the guide block, the needle can be inserted through the bore in the needle guide and into the tissue on the lateral side of the knee bone until a distal tip of the needle abuts an outer surface of the knee bone. Prior to positioning the guide block and prior to adjusting the trajectory of the bore extending through the guide block, a first end of a medial-lateral arc of the cross pinning guide device can be mated to the guide block, a second end of the medial-lateral arc including the needle guide. After adjusting the trajectory of the bore extending through the guide block, a cross pin can be advanced through the bore extending through the guide block and into a medial-lateral bone tunnel extending into the medial side of the knee bone such that the cross pin intersects a proximal-distal bone tunnel formed in the knee bone.

The method can vary in any other number of ways. The method can include inserting a guide rod coupled to the guide block into a bone tunnel formed in the knee bone, and, with the guide rod inserted into the bone tunnel, rotating the cross pinning guide device about a longitudinal axis of the bone tunnel. The method can include determining the insertion depth of the needle based on a position of a mark on the needle relative to the bore in the needle guide.

In another embodiment, a surgical method is provided that includes preparing a femoral tunnel using an anteromedial approach through a joint space between a femur and a tibia and into the femur, inserting a femoral guide rod of a guide system into the femoral tunnel, positioning a frame extending from the femoral guide rod on a medial side of the femur, positioning a needle guide on a gauge assembly coupled to the frame on a lateral side of the femur, inserting a needle through the needle guide and through tissue to contact a lateral surface of the femur, the needle having a depth indicator that indicates a distance between the lateral surface of the femur and a target location of a distal end of a cross pin to be implanted in the femur, adjusting a trajectory of at least one bore extending through a guide block mounted on an arc of the frame, advancing a drill through the at least one bore in the guide block and into the medial side of the femur to form a pilot hole in the medial side of the femur that intersects the femoral tunnel, positioning a ligament graft within the femoral tunnel, and delivering a cross pin through the pilot hole such that the cross pin engages the ligament graft to thereby secure the ligament graft within the femoral tunnel.

BRIEF DESCRIPTION OF THE DRAWINGS

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

FIG. 3 is a top perspective view another embodiment of a frame and guide block, with an adaptor mated to the frame, and with drills and drill sleeves inserted through the guide block;

FIG. 4 is a bottom perspective view of the frame, guide block, adaptor, drills, and drill sleeves of FIG. 3;

FIG. 7 is a side view of one embodiment of a drill sleeve and one embodiment of a drill configured to be inserted through the drill sleeve;

FIG. 8 is a top proximal view of the drill sleeve of FIG. 7;

FIG. 9 is a perspective view of another embodiment of a drill sleeve with the drill of FIG. 7 inserted therethrough;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Various exemplary methods and devices are disclosed for implanting a cross-pin through a bone tunnel, such as in an arthroscopic surgical procedure. In general, the methods and devices allow a cross-pin hole to be formed in a medial side of a knee bone such that it intersects a bone tunnel formed in the knee bone. In an exemplary embodiment, a cross-pinning guide device is provided that can be configured to angularly position the cross-pin hole relative to the bone tunnel to allow the cross-pin hole to intersect the bone tunnel without passing through another side, e.g., a lateral side, of the knee bone, thereby reducing trauma to the knee and facilitating healing. The knee bone can be a femur or a tibia such that the cross-pin hole and the bone tunnel can each be entirely formed in the femur or in the tibia. The methods and devices can reduce chances of damaging bone during the surgical procedure because the tibia and the femur do not both need to be drilled to form a bone tunnel and/or a cross-pin hole in each of the tibia and the femur. Because the bone tunnel and the cross-pin hole can each be entirely formed in the same knee bone, e.g., in one of the femur and the tibia, surgical instruments do not need to be passed through much, if any, cartilage located between the femur and tibia, thereby reducing chances of damaging the delicate cartilage during the surgical procedure.

Figure 1:
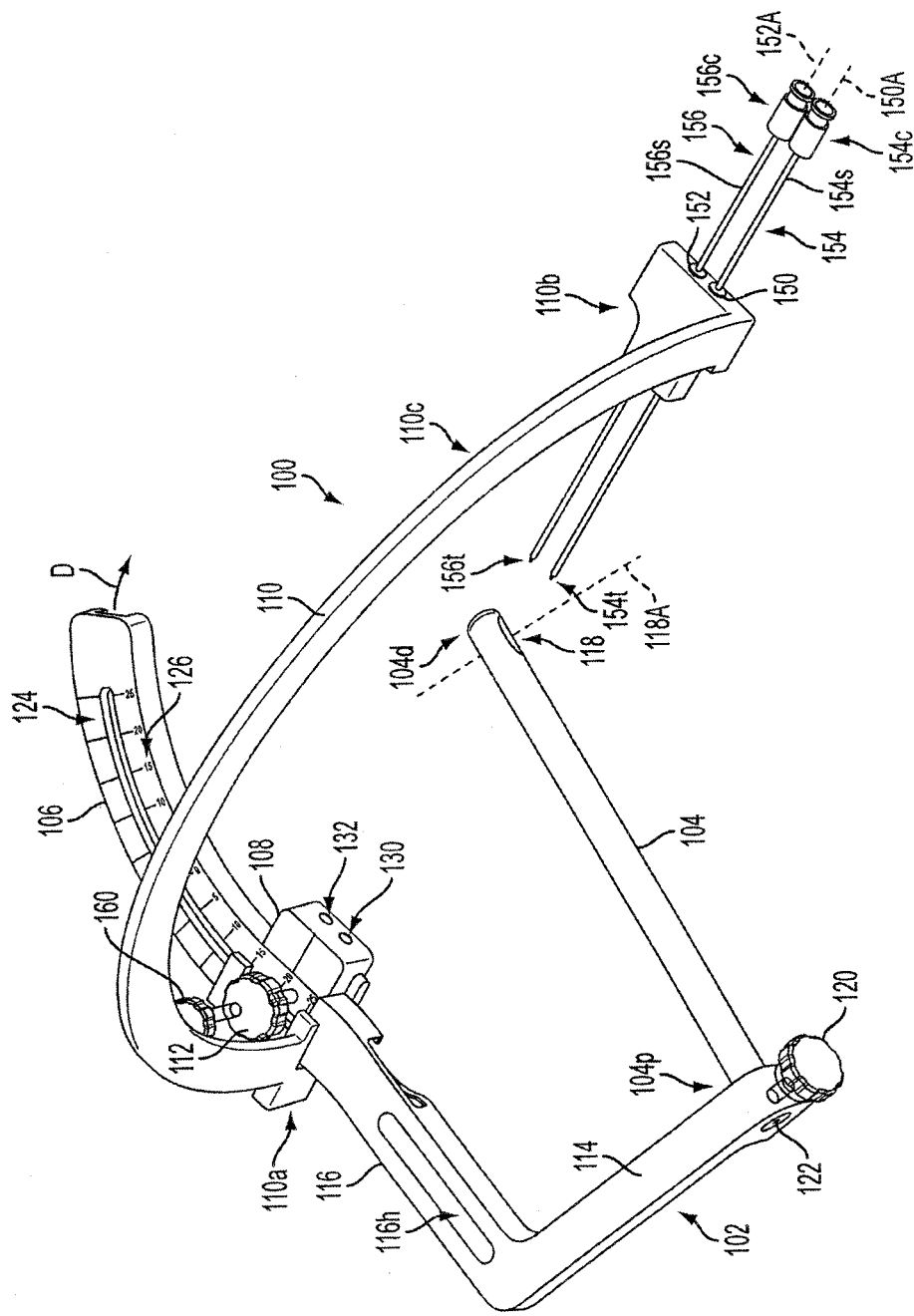
FIG. 1 is a perspective view of one embodiment of a cross pinning guide device including a frame, a guide block mated to the frame, and a medial-lateral arc mated to the guide block, with two needles inserted through an end of the medial-lateral arc.
Figure 2:
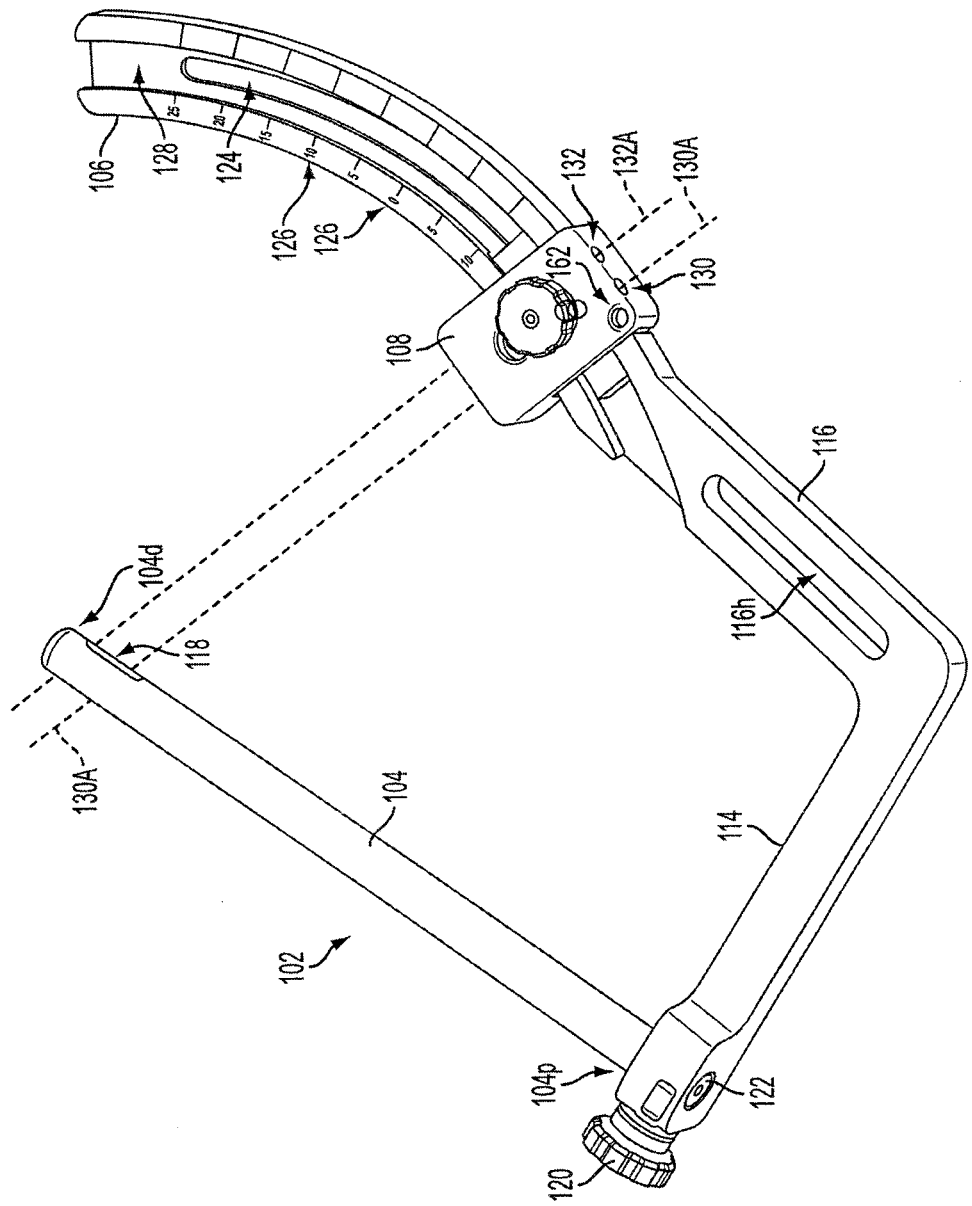
FIG. 2 is a perspective view of the frame and guide block of FIG. 1.

FIG. 1 illustrates one exemplary embodiment of a cross-pinning guide device 100 configured to aid in cross-pinning a ligament graft in a bone tunnel, e.g., a femoral tunnel or a tibial tunnel. The device 100 can include a frame 102 having a guide rod 104 and a proximal-distal arc 106, referred to herein as the "proximal-distal arc" or "first arc," spaced a distance apart from the guide rod 104. The device 100 can also include a guide block 108 and a medial-lateral arc 110. The guide block 108 can be configured to slidably couple to the frame 102, e.g., to the first arc 106, as illustrated in FIG. 1, such that the guide block 108 can be slidably movable along the frame 102, e.g., along the first arc 106, relative thereto. The guide block 108 can be configured to be locked at a selected position along the first arc 106, such as with a first thumbscrew 112, as discussed further below. The medial-lateral arc 110, referred to herein as the "medial-lateral arc" or "second arc," can be configured to detachably mate to the guide block 108 such that the first arc 106 can be positioned in a first plane, and the second arc 110 can be positioned in a second plane substantially perpendicular to the first plane, as illustrated in FIG. 1 with the second arc 110 mated to the frame 102. FIG. 1 shows the second arc 110 mated to the frame 102 at the guide block 108, which is shown in FIG. 1 slidably mated to and locked along the first arc 106 of the frame 102. FIG. 2 shows the guide block 108 slidably mated to and unlocked along the frame 102 without the second arc 110 being mated to the frame 102.

The frame 102 can have a variety of configurations. As in the illustrated embodiment, the frame 102 can include the guide rod 104, an L-shaped member having a base portion 114, and an arm portion 116 extending transversely to, e.g., substantially perpendicular to, the base portion 114. A terminal end of the base portion 114 can be configured to mate to a terminal end of the guide rod 104, and the arm portion 116 can be configured to mate to the guide block 108.

As in the illustrated embodiment, the guide rod 104 can include a substantially cylindrical shaft having an opening 118 formed in a distal portion thereof. The opening 118 can, as in the illustrated embodiment, extend through opposed sides of the guide rod 104, although in some embodiments, the opening 118 can be formed as a blind hole formed partially through the guide rod 104. The opening 118 can be in the shape of an elongate slot and can have any longitudinal length along the guide rod's longitudinal length. The guide rod 104 can be a solid member, or it can be cannulated along its longitudinal length. Cannulation of the guide rod 104 can allow for placement of the guide rod 104 on a guide wire (not shown). Although a distal end 104d of the guide rod 104 is rounded in the illustrated embodiment, the distal end 104d can have a variety of shapes, e.g., conical, flat or planar, beveled, etc. A guide rod 204 of FIGS. 3 and 4, discussed further below, includes a beveled distal end.

The guide rod 104 can be configured to mate to the base portion 114 of the frame 102 such that, as shown in FIG. 1, the guide rod opening 118 is spaced a distance away from the base portion 114 along a longitudinal length of the guide rod 104, the guide rod 104 is spaced a distance apart from the arm portion 116 of the frame 102, and the first arc 106 extends in a direction substantially parallel to a direction of the guide rod 104. With the guide rod 104 mated to the base portion 114, as shown in FIG. 1, the opening 118 can be oriented relative to the base portion 114 such that an axis 118A passing into or through the opening 118 is substantially parallel to the base portion 114 and substantially perpendicular to the arm portion 114.

In an exemplary embodiment, the guide rod 104 can be configured to detachably mate to the base portion 114 of the frame 102 by mating a proximal end 104p of the guide rod 104 to an end of the base portion 114, e.g., by inserting the proximal end 104p of the guide rod 104 into a corresponding hole 122 formed in the base portion 114. The guide rod 104 can be configured to be locked in a mated position relative to the base portion 114, e.g., by snap fit, matable threads, a second thumbscrew 120 as in the illustrated embodiment, etc. The guide rod 104 and the base portion 114 can be configured to be matable in a predetermined orientation relative to one another, e.g., by keying, visual marking, etc., to facilitate proper orientation of the guide rod's opening 118 relative to the arm portion 116 when the guide rod 104 is mated to the base portion 114. Providing a detachable guide rod can facilitate cleaning of the guide rod 104 and the frame 102. The frame 102 can be provided as part of a kit including the detachable guide rod 104 as one of a plurality of guide rods each configured to detachably mate to the frame 102. The plurality of guide rods can have a variety of longitudinal lengths and diameters to accommodate various graft sizes and patient anatomies. In some embodiments, a proximal end of the guide rod 104 can be nonremovably mated to the end of the base portion 114. If the guide rod 104 is nonremovably mated to the frame 102, the frame 102 can be provided as part of a kit including a plurality of frames, each frame having differently sized guide rods nonremovably mated thereto.

The guide rod 104 as illustrated in the embodiment of FIG. 1 is mated to the base portion 114 as a femoral guide rod configured to be inserted into a bone tunnel formed in a femur, as discussed further below. The guide rod 104 can also be mated to the base portion 114 as a tibial guide rod configured to be advanced into a bone tunnel formed in a tibia. However, due to differences in femur and tibial anatomy, mating the guide rod 104 directly to the base portion 114, as shown in FIG. 1, can present difficulties in properly orienting the frame 102 relative to a tibia if the surgical procedure involves forming a bone tunnel in the tibia in which the guide rod 104 is to be inserted. FIGS. 3 and 4 illustrate a guide rod 204 mated to a base portion 214 of a frame 204, via an adaptor 201. A proximal end of the adaptor 201 can be configured to detachably mate to or be integrally formed with an end of the base portion 214, and a proximal end of the guide rod 204 can be configured to detachably mate to or be integrally formed with a distal end of the adaptor 201. In this way, the adaptor 201 can allow the same base portion 214 and the same guide rod 204 to be used whether a bone tunnel is being formed in the femur (not using the adaptor 201) or in the tibia (using the adaptor 201), which can reduce a number of guide rods and/or base portions that need to be provided as part of a surgical kit.

Referring again to FIGS. 1 and 2, the arm portion 116 can include a proximal portion extending from the base portion 114, and a distal portion including the first arc 106. The first arc 106 can have an arcuate shape having an inner concave surface facing the guide rod 104, when the guide rod 104 is mated to the base portion 114, such that the first arc 106 can arc at a terminal end thereof in a direction D toward the guide rod 104. As in the illustrated embodiment, the first arc 106 can include a ruled scale, e.g., a plurality of angle degree marks 126, along at least a portion of its longitudinal length. The marks 126 can facilitate precise positioning of the guide block 108 along the first arc 106, as discussed further below. Although the marks 126 in the illustrated embodiment are in five degree increments from −25 degrees to 25 degrees, the marks 126 can span any range and can have any increment. The first arc 106 can include the marks 126 on opposed sides thereof, as shown in the embodiment of FIGS. 1 and 2, which can facilitate use of the frame 102 with both the left and right knees.

The arm portion 116 can include one or more holes 116h formed therein, as in the illustrated embodiment. The holes 116h can be used to improve visibility of a surgical site, aid gripping of the frame 102, and/or help reduce a weight of the frame 102, which can help make the frame 102 easier to transport and to use during a surgical procedure. In addition to or as an alternative to the arm holes 116h, the base portion 114 can include one or more holes formed therein.

As further shown in FIGS. 1 and 2, the first arc 124 can have a groove 128 formed therein, which can facilitate smooth sliding of the guide block 108 along the first arc 106. The groove 128 can be formed on one of the opposed sides of the first arc 106, e.g., on one of the sides including the marks 126, although any side(s) of the first arc 106 can have a groove. In addition or in alternative to the groove 128, the first arc 106 can include a longitudinal opening or slot 124 formed therein and extending through both opposed surfaces thereof. As in the illustrated embodiment, the slot 124 can be formed in a portion of the groove 128. The groove 128 and the slot 124 can be configured to facilitate sliding of the guide block 108 along the first arc 106 and locking the guide block 108 relative thereto, as discussed further below.

The guide block 108 can have a variety of configurations. The guide block 108 can be configured to be detachably, slidably matable to the frame 102, or as in this illustrated embodiment, the guide block 108 can be configured to be nonremovably, slidably mated to the frame 102, e.g., to the first arc 106. The groove 128 and the slot 124 can be configured as guide paths for the guide block 108 along the first arc 106 to facilitate smooth sliding thereof. The guide block 108 can be configured to selectively slide proximally and distally along the first arc 106. As mentioned above, the guide block 108 can be locked at a particular position along the first arc 106. The first thumbscrew 112 can be configured to move between an unscrewed configuration, in which the guide block 108 can slide along the first arc 106, and a screwed configuration, in which the guide block 108 is locked at the particular position along the first arc 106 and cannot slide along the first arc 106. In use, as discussed further below, when the guide block 108 is at a desired position along the first arc 106, e.g., at a desired angular orientation as indicated by the marks 126, the first thumbscrew 112 can be moved from the unscrewed configuration to the screwed configuration to lock the guide block's position. The first thumbscrew 112 can move between the unscrewed and screwed configurations any number of times during a surgical procedure. Similarly, the guide block 108 can be slid any number of times and any distance proximally and/or distally along the first arc 106.

The guide block 108 can have at least one bore formed therethrough that is configured to receive an instrument, e.g., a cross pin, a drill, a drill sleeve configured to receive a drill, etc. In an exemplary embodiment, longitudinal axes of each of the one or more bores can be parallel to one another to allow instruments that are inserted therethrough to be parallel to one another. Each of the one or more bores can be longitudinally formed through the guide block 108 such that when the guide block 108 is mated to the first arc 106, longitudinal axes of each of the bores can be substantially perpendicular to a longitudinal axis of the arm portion 116. In the illustrated embodiment, the guide block 108 has first and second bores 130, 132 formed therethrough. As in the illustrated embodiment, the first and second bores 130, 132 can be spaced equidistantly from a horizontal center H1 of the guide block 108. In another embodiment, the first and second bores 130, 132 can additionally or alternatively be centered vertically in the guide block. The illustrated bores 130, 132 are cylindrical, but the bores 130, 132 can have any shape. As shown in FIG. 2, with the guide rod 104 mated to the base portion 114, the first and second bores 130, 132 can have first and second longitudinal axis 130A, 132A, respectively, that are parallel to one another and that pass through the opening 118 of the guide rod 104. In this way, first and second instruments inserted through the first and second bores 130, 132, respectively, can be parallel to one another and can intersect the guide rod opening 118, thereby ensuring that instruments inserted through the bores 130, 132 toward the guide rod 104 can pass through the opening 118. Regardless of the location of the guide block 108 along the first arc 106, the guide block 108 can be configured such that the first and second longitudinal axis 130A, 132A always pass through the opening 118 of the guide rod 104.

Figure 6:
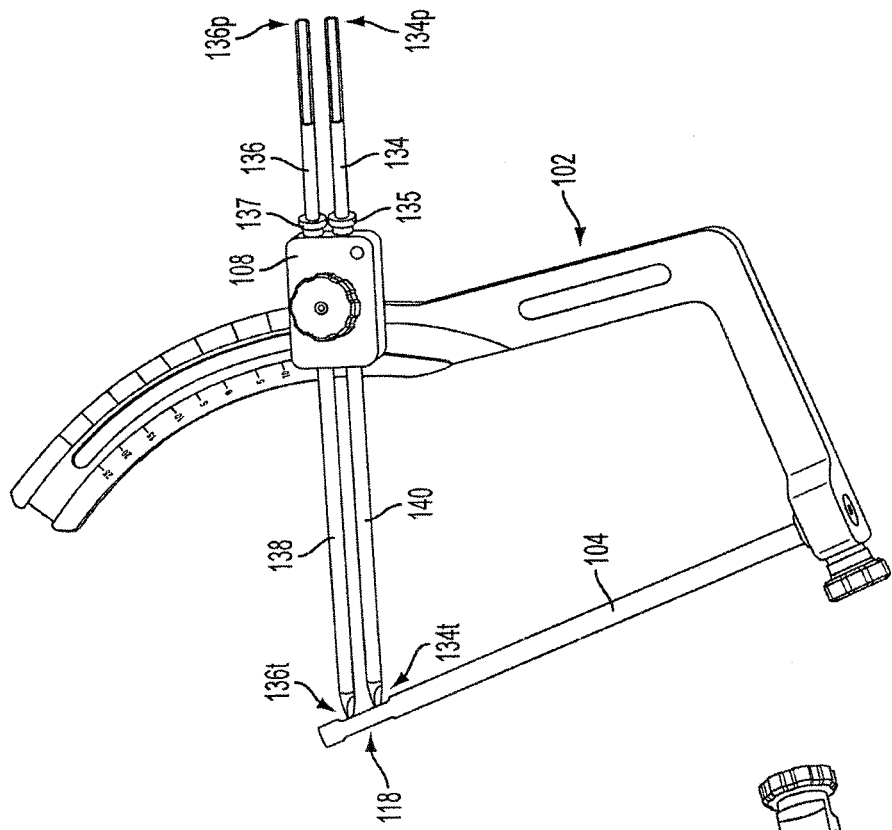
FIG. 6 is a top perspective view of the frame, guide block, and adaptor of FIG. 5.
Figure 5:
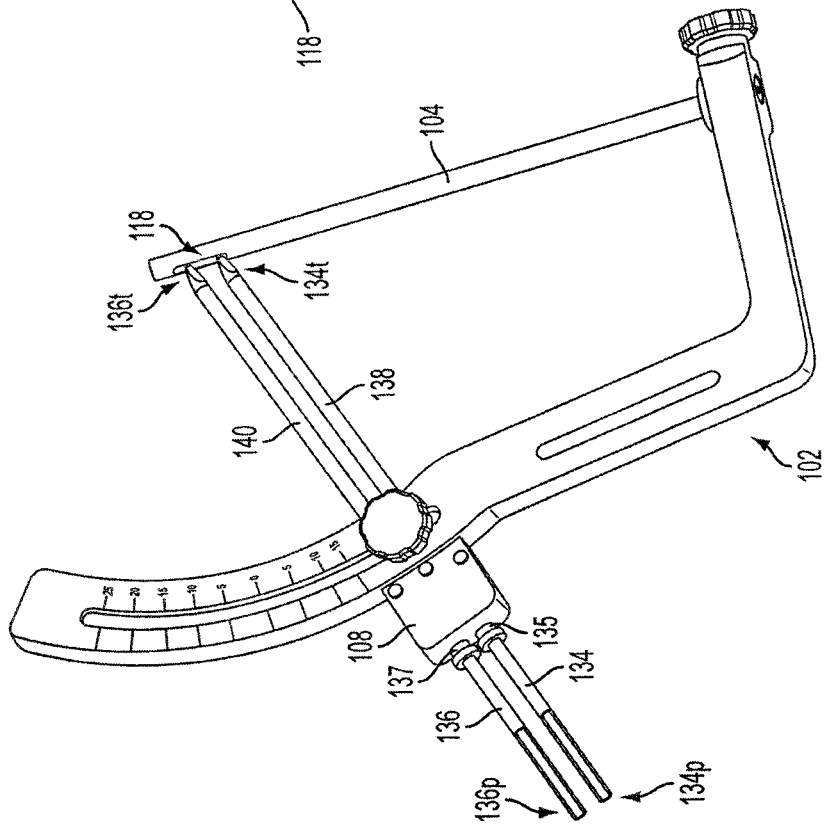
FIG. 5 is a bottom perspective view of the frame and guide block of FIG. 1, with drills and drill sleeves inserted through the guide block.

As shown, for example, in FIGS. 5 and 6, first and second drills 134, 136 can be inserted through the first and second bores 130, 132, respectively, to intersect the guide rod opening 118. The first and second drills 134, 136 can have a variety of configurations. Generally, the first and second drills 134, 136 can be substantially rigid members and can be configured to form bone tunnels in bone when inserted therein. As illustrated, the first and second drills 134, 136 can have sharp tips 134t, 136t for penetrating and/or cutting bone. As also shown in FIG. 7, the first and second drills 134, 136 can include first and second transversely-extending pins 135, 137, respectively, extending from shafts thereof. The first and second pins 135, 137 can be positioned anywhere along longitudinal lengths of the drills 134, 136, but in an exemplary embodiment, the pins 135, 137 are located in proximal portions of the drills 134, 136 a distance distal from proximal-most ends 134p, 136p of the drills 134, 136, e.g., a first distance 135D for the first drill 134 illustrated in FIG. 7. Although the pins 135, 137 can extend in one direction from sides of the drills 134, 136, in an exemplary embodiment, the pins 135, 137 can extend from two sides of the drills 134, 136 as in the illustrated embodiment. The pins 135, 137 can be formed in any way, such as each including two pin extensions on opposed sides of the drills 134, 136, or each including a single pin extending through the drills to extend from opposed sides of the drills.

The first and second drills 134, 136 are shown in FIGS. 5 and 6 as being respectively disposed in first and second drill sleeves 138, 140 inserted through the first and second bores 130, 132 of the guide block 108 prior to disposal of the drills 134, 136 in the sleeves 138, 140. However, one or both of the first and second drills 134, 136 can be inserted directly through the first and second bores 130, 132, respectively, e.g., without drill sleeves. Additionally, although two drills 134, 136 are illustrated in FIGS. 5 and 6 as being inserted through the guide block 108, in some embodiments, only one drill can be inserted through one of the guide block's bores 130, 132 so as to form only one bone tunnel.

The drill sleeves 138, 140 can also have a variety of configurations. As in the illustrated embodiment, the drill sleeves 138, 140 can each be substantially rigid members and can each include cannulated shafts configured to receive an instrument, e.g., a drill, therein. The drill sleeves 138, 140 and the drills 134, 136 can have any longitudinal lengths. In an exemplary embodiment, the drills 134, 136 have longitudinal lengths greater than their respective drill sleeves 134 such that, as shown in FIGS. 5 and 6, the drills 134, 136 can be received within their respective drill sleeves 138, 140 and have portions extending beyond both ends of the drill sleeves 138, 140. In other words, when the drills 134, 136 are inserted through the sleeves 138, 140, the distal tips 134t, 136t can be positioned distally beyond distal-most ends of the sleeves 138, 140, and the proximal-most ends 134p, 136p of the drills can be positioned proximally beyond proximal-most ends of the sleeves 138, 140. When inserted through the bores 130, 132, the drill sleeves 138, 140 can be configured to be axially and rotatably movable in their respective bores 130, 132.

As shown in FIGS. 5-8, the first and second drill sleeves 138, 140 can include first and second proximal collar portions 142, 144, respectively, having diametrically extending first and second slots 145, 147 respectively formed therein. The first and second slots 145, 147 can be configured to receive the drills' first and second pins 135, 137, respectively. When the first and second drills 134, 136 are respectively inserted into the drill sleeves 138, 140, the first and second drills 134, 136 can be advanced distally therein until the first and second pins 135, 137 are respectively seated in the first and second slots 145, 147, as illustrated in FIGS. 5 and 6. In this way, axial movement of one or both of the drills 134, 136 in a distal direction can cause corresponding axial movement in their related one of the drill sleeves 138, 140. Similarly, rotational movement of one or both of the drills 134, 136 about its longitudinal axis can cause corresponding rotational movement of their related one of the drill sleeves 138, 140. Such cooperative movement of the drills 134, 136 and drill sleeves 138, 140 can facilitate formation of bone tunnels. As discussed further below, in an exemplary embodiment, at least the drills 134, 136, if not also the drill sleeves 138, 140, can be drilled far enough into bone to enter the guide rod opening 118 already positioned in a bone tunnel formed in the bone.

In another embodiment, a proximal collar portion of a drill sleeve can include at least one contact surface configured to engage a pin of a drill. In an exemplary embodiment, illustrated in FIG. 9, a drill sleeve 138' can include a proximal collar portion 142' having two opposed contact surfaces 143, each configured to engage a pin extending from a drill, e.g., the pin 135 extending from opposed sides of the first drill 134. In this way, when the drill 134 is inserted through the drill sleeve 138' such that the pin 135 engages the contact surfaces 143, axial movement of the drill 134 in a distal direction can cause corresponding axial movement in the drill sleeve 138', and rotational movement of the drill 134 in a clockwise direction about its longitudinal axis can cause corresponding rotational movement of the drill sleeve 138' in a clockwise direction. The drill sleeve 138' is configured to respond to clockwise rotational movement of the drill 134, the proximal collar portion 142' can be similarly configured to respond to counterclockwise rotational movement.

Figure 10:
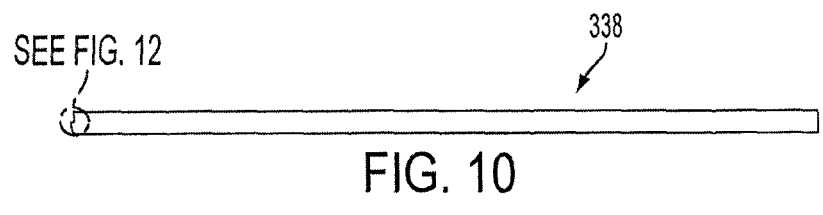
FIG. 10 is a side view of yet another embodiment of a drill sleeve.
Figure 11:
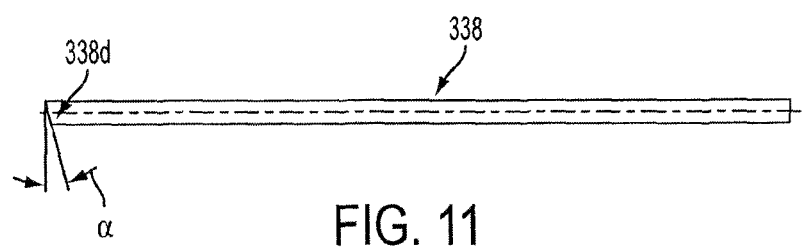
FIG. 11 is another side view of the drill sleeve of FIG. 10.
Figure 12:
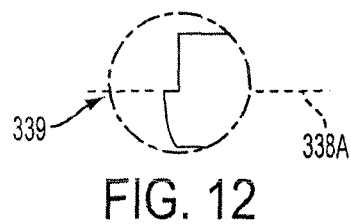
FIG. 12 is a side view of a distal end of the drill sleeve of FIGS. 10 and 11.

The distal ends of the sleeves 138, 140 can include flat tips, as shown in FIGS. 5-7. However, one or all of the drill sleeves 138, 140 can have other distal end configurations, such as rounded or conical. In an exemplary embodiment, drill sleeves inserted through the guide block's bores 130, 132 can have distal ends including one or more cutting teeth. The cutting teeth can be configured to enhance cutting performance of the drill sleeve and to reduce an axial force needed for the cutting, such as when creating a bone tunnel. FIGS. 10-12 illustrate one embodiment of a drill sleeve 338 including one cutting tooth 339, although as mentioned above, the drill sleeve 338 can include a plurality of teeth. The tooth 339 can extend distally from the drill sleeve 338 such that a distal-most edge 338d of the drill sleeve 338 can be asymmetric about its longitudinal axis 338A, as shown in FIG. 12. The distal-most edge 338d of the drill sleeve 338 can be angled at an angle α, e.g., about 5 degrees, and can be sharp all around, which can also facilitate cutting.

One or all of the drill sleeves 138, 140 can have a lubricated coating on its outer surface, inner surface, and/or on any other portions of the drill sleeves 138, 140. The lubricated coating can be formed on drill sleeves in any way, such as by fully dipping the drill sleeves in a validated Siliconization process. The lubricated coating can help facilitate smooth drilling bone holes, facilitate sleeve removal from bone, reduce heat generation during drilling, and/or reduce the potential for galling between bone and the sleeve, between the sleeve and a instrument inserted through and the sleeve, and between the sleeve and the guide block. The coating can include any biocompatible lubricated coating, but in an exemplary embodiment, the coating can include Dow Corning® 630 Medical Fluid, available from Dow Corning Corporation of Midland, Mich.

Figure 13:
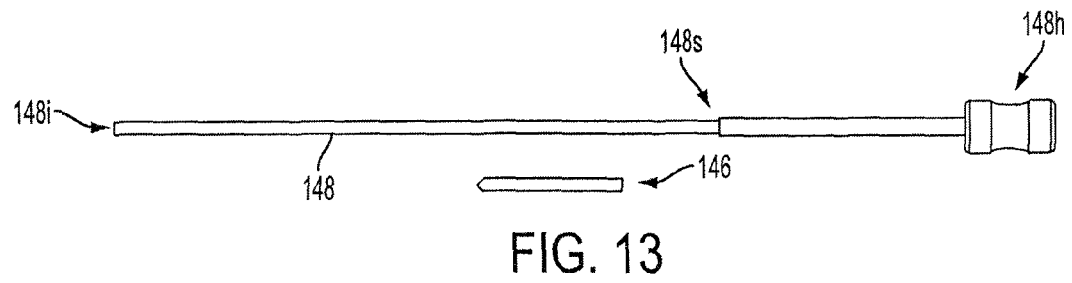
FIG. 13 is a side view of one embodiment of an insertion tool and one embodiment of a cross pin configured to be inserted into a patient using the insertion tool.

As mentioned above, the first and second bores 130, 132 can be configured to receive instruments other than drills and drill sleeves, such as cross pins. The cross pins can have a variety of configurations, and can be inserted into a patient in any way. The cross pins can be formed from one or more materials, such as a polymeric, a bioceramic, a composite, a non-absorbable material, etc. In an exemplary embodiment, the cross pins are formed of a bio-absorbable material, e.g., poly(lactic acid) with tri-calcium phosphate and copolymer of lactide and glycolide (poly(lactide-co-glycolide)) with tri-calcium phosphate. An exemplary embodiment of a cross pin 146 is illustrated in FIG. 13.

The cross pins can be inserted directly through the bores 130, 132, but in an exemplary embodiment, the cross pins can be inserted through insertion tools inserted through the bores 130, 132. The insertion tools can be directly inserted through the bores 130, 132, or similar to the drills 134, 136, can be inserted through sleeves, e.g., the drill sleeves 138, 140, inserted through the bores 130, 132. The insertion tools can have a variety of configurations. FIG. 13 illustrates an exemplary embodiment of such an insertion tool 148 configured to be slidably inserted through one of the bores 130, 132 and to have the cross pin 146 advanced therethrough. The insertion tool 148 can have a cross-pin insertion tip 148i, a handle 148h that can be struck with a mallet for inserting the cross pin 146 therethrough, and a step-in diameter 148s for controlling a depth of insertion of the cross pin 146.

Although FIGS. 3 and 4 illustrate the drill sleeves 138, 140 and the drills 134, 136 inserted through the guide block's bores 130, 132 without the medial-lateral or second arc 110 being attached to the guide block 108 (FIGS. 5 and 6 similarly illustrate drill sleeves and drills so inserted through bores of a guide block), the drill sleeves 138, 140, the drills 134, 136, and/or any other instruments can be inserted through the guide block's bores 130, 132 with the second arc 110 attached to the guide block 108. In other words, when the second arc 110 is mated to the guide block 108, the second arc 110 will not obstruct the bores 130, 132. In this way, the guide block 108 and the guide block's bores 130, 132 can cooperate with the second arc 110 to facilitate cross pinning.

Figure 14:
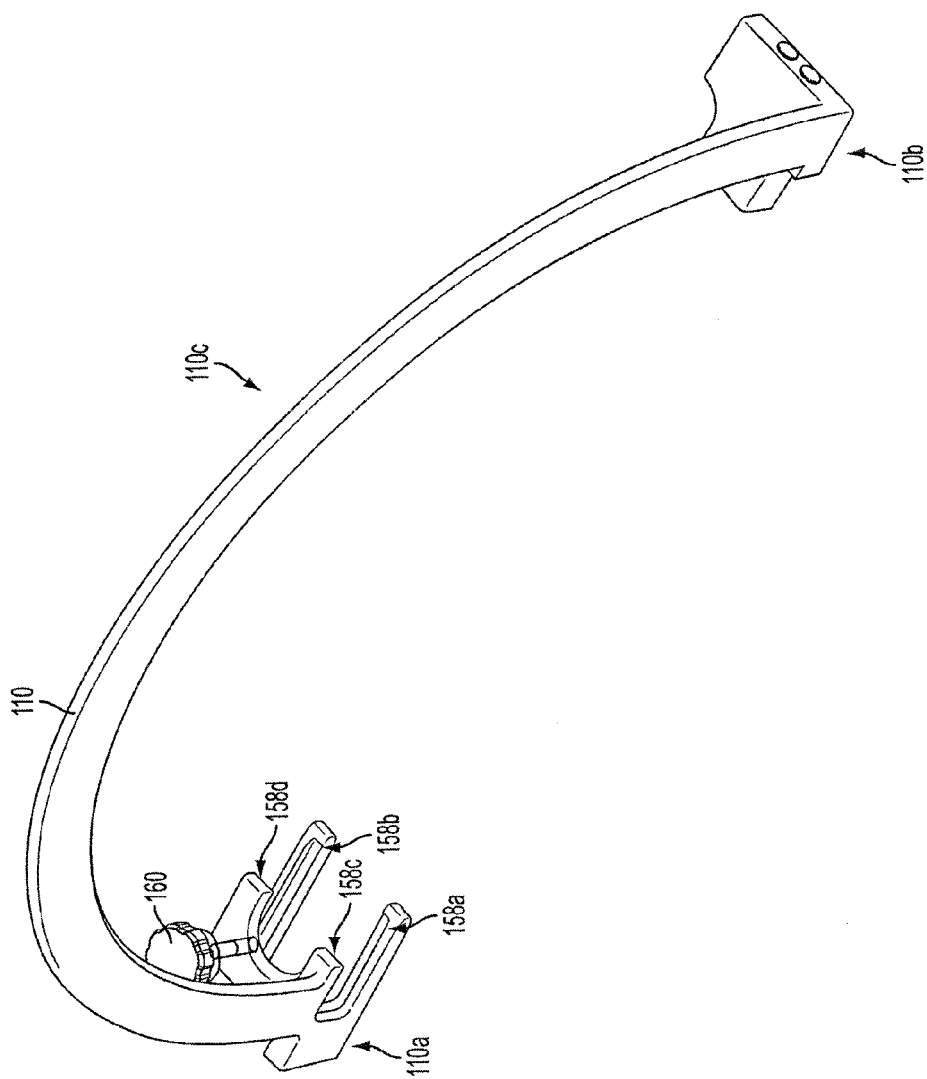
FIG. 14 is a perspective view of the medial-lateral arc of FIG. 1.
Figure 15:
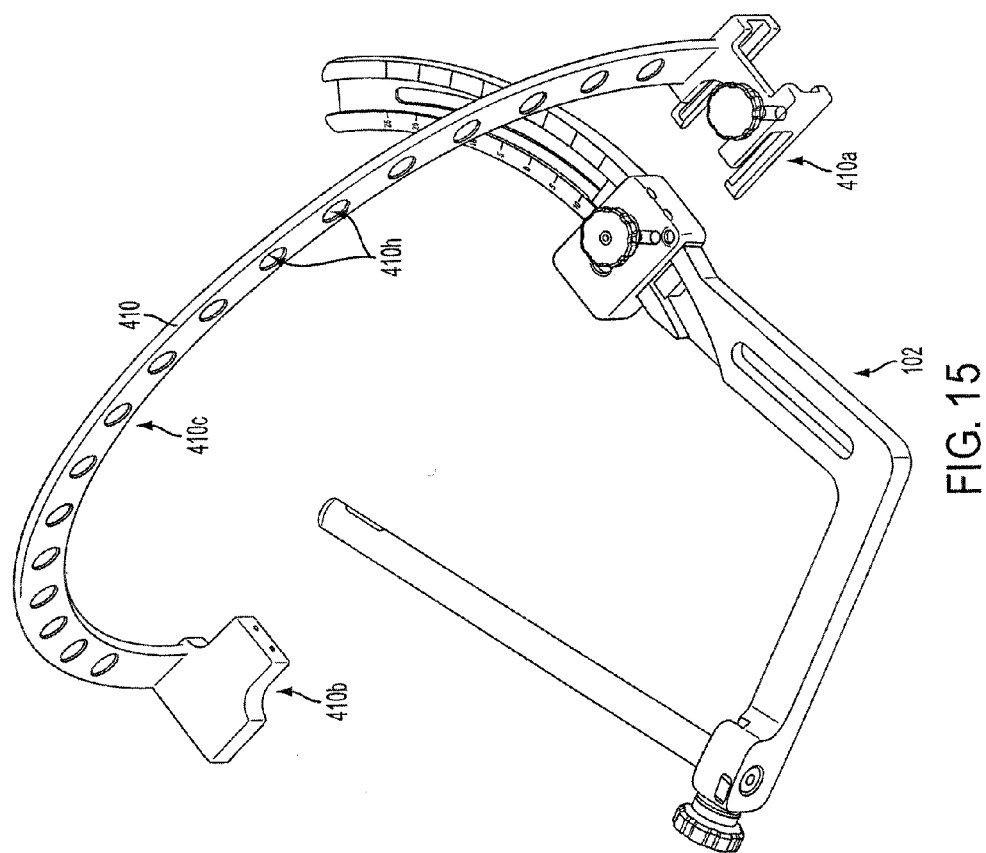
FIG. 15 is a perspective view of the frame and guide block of FIG. 1, and another embodiment of a medial-lateral arc configured to mate to the guide block.

The second arc 110 can have a variety of configurations. As in the illustrated embodiment of FIG. 1, the second arc 110, also shown in FIG. 14, can including a first end 110a and a second end 110b with an arcuate portion 110c extending therebetween. The arcuate portion 110c can be a solid member as shown in the embodiment of FIG. 1, or it can be at least partially hollow and/or include one or more holes formed therein. FIG. 15 illustrates an embodiment of a medial-lateral or second arc 410 including a first end 410a and a second end 410h with an arcuate portion 410c extending therebetween and having a plurality of holes 410h formed therein. Similar to the holes 116h of the arm portion 116 discussed above, the holes 410h of the arcuate portion 410 can be used to improve visibility of a surgical site, aid gripping of the arcuate portion 410, and/or help reduce a weight of the arcuate portion 410.

Referring again to FIGS. 1 and 14, the first end 110a of the second arc 110 can be configured in a variety of ways to detachably mate to the guide block 108. Generally, the second arc 110 can include an engagement mechanism configured to detachably mate the second arc 110 to the guide block 108. As in the illustrated embodiment, the second arc's engagement mechanism can include at least one track, e.g., first, second, third, and fourth tracks 158a, 158b, 158c, 158d formed in the first end 110a, that is configured to slidably engage the guide block 108. The at least one track can be configured to slidably engage at least one rail of the guide block 108, or, as in the illustrated embodiment, the four tracks 158a, 158b, 158c, 158d can be configured to seat the four corner edges of the substantially rectangular guide block 108 so as to seat the guide block 108 in the tracks 158a, 158b, 158c, 158d. In another embodiment, the second arc can include at least one rail configured to engage at least one track of the guide block.

With the second arc's engagement mechanism engaging the guide block 108, the second arc 110 can be configured to be locked in a fixed position relative thereto. The second arc 110 can lock to the guide block 108 in a variety of ways, such as by snap fit, matable threads, a depressible button, etc. As in the illustrated embodiment, the first end 110a of the second arc 110 can include a third thumbscrew 160 configured to be pushed and/or screwed into a corresponding bore 162 formed in the guide block 108, shown in FIG. 2, to lock the second arc 110 in a nonslidable, fixed position relative to the guide block 108.

Figure 16:
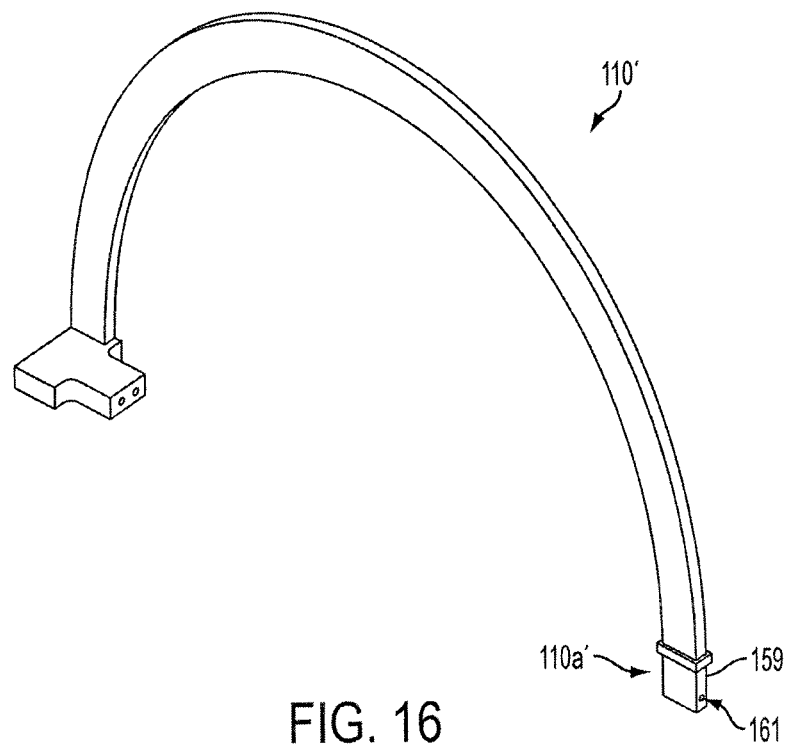
FIG. 16 is a perspective view another embodiment of a medial-lateral arc.

Another embodiment of an engagement mechanism configured to detachably mate a medial-lateral or second arc to a guide block includes a male member at a first end of the second arc. The male member can be configured to be received in a female member formed in the guide block. With the second arc's male member seated in the guide block's female member, the second arc can be configured to be locked in a fixed position relative thereto. The second arc can lock to the guide block in a variety of ways, such as by snap fit, matable threads, a depressible button, etc. FIG. 16 shows an embodiment of an engagement mechanism in the form of a male member 159 at a first end 110a' of a medial-lateral or second arc 110'. The male member 159 can be configured to be received in a female member formed in a guide block. With the second arc's male member 159 seated in the guide block's female member, the second arc 110' can be configured to be locked in a fixed position relative thereto, such as by using a depressible protrusion 161 configured to be engage, such as by releasable snap fit, a corresponding depression or hole formed in the guide block.

Figure 17:
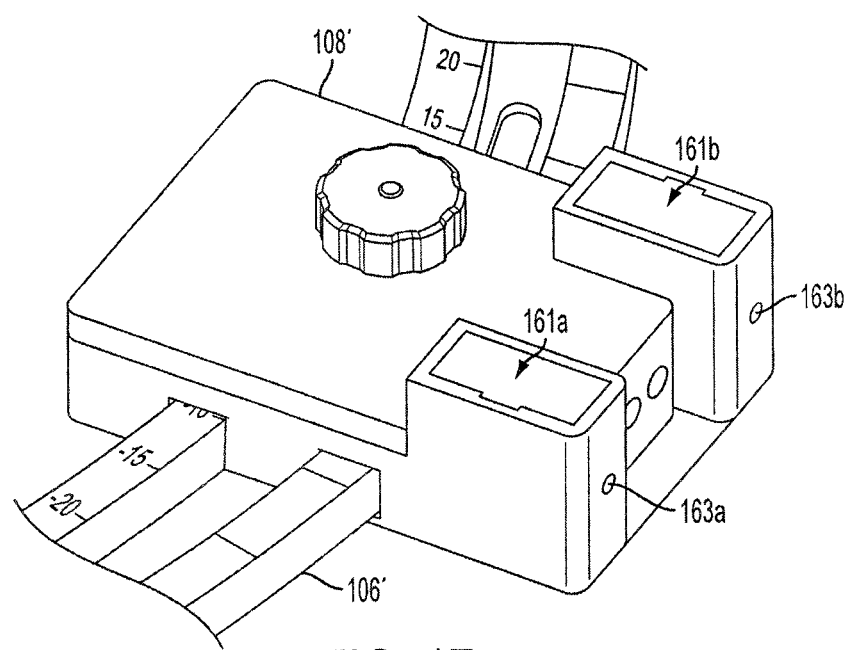
FIG. 17 is a perspective view of another guide block configured to mate to the medial-lateral arc of FIG. 16, the guide block being mated to a proximal-distal arc of a frame.

The guide block can include one or more female members, each configured to receive a male member of a second arc. In an exemplary embodiment, the guide block can include two female members, each keyed to receive a correspondingly keyed male member of a second arc. The keying can prevent the second arc from connecting to the guide block in a wrong orientation. In addition or alternative to keying, the male and female members can be otherwise configured to be specifically related to one another, such as by visual marking. In this way, a frame having the guide block mated thereto can be used for both the left and right knees, with one female member being configured to receive a male member of a second arc for use with the left knee, and the other female member being configured to receive another male member of another second arc for use with the right knee. FIG. 17 illustrates one embodiment of a guide block 108' mated to a medial-lateral or first arc 106' and including first and second female members 161a, 161b. Each of the female members 161a, 161b can, as shown in this embodiment, be keyed. One of the female members 161a, 161b, e.g., the first or left-side female member 161a, can be keyed to receive a male member of a second arc configured for use on the left knee, and the other of the female members 161a, 161b, e.g., the second or right-side female member 161b, can be keyed to receive another male member of another second arc, e.g., the second arc 110' of FIG. 16 (its key feature is obscured on the hidden wider side of the male member 159), configured for use on the right knee. The female members 161a, 161b in this illustrated embodiment also each include a hole 163a, 163b formed in a wall of the guide block 108' that can be configured to receive a corresponding protrusion of a male member to releasably lock the male member therein.

Figure 18:
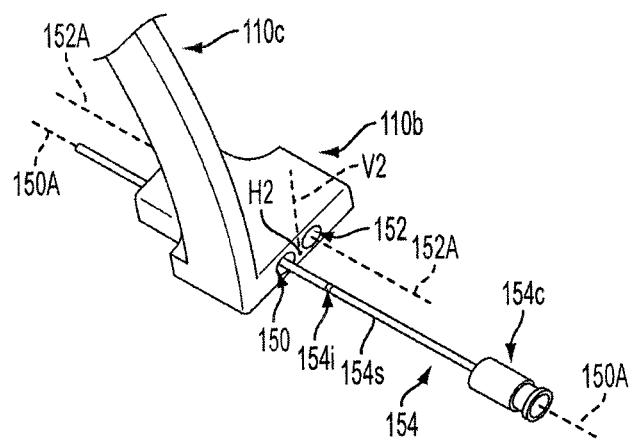
FIG. 18 is a perspective view of one of the needles of FIG. 1 inserted through the end of the medial-lateral arc.

Referring again to the embodiment of FIG. 1, a needle guide can be at the second end 110b of the second arc 110, also shown in FIG. 18, and have at least one bore, e.g., first and second bores 150, 152, formed therethrough. As in the illustrated embodiment, the first and second bores 150, 152 can be spaced equidistantly from a horizontal center H2 of the second end 110b and can be centered vertically V2 in the second end 110b. The illustrated bores 150, 152 are cylindrical, but the bores 150, 152 can have any shape. As in the illustrated embodiment, with the guide rod 104 mated to the base portion 114, the first and second bores 150, 152 can have first and second longitudinal axes 150A, 152A, respectively, that are parallel to one another and that pass through the opening 118 of the guide rod 104. In this way, first and second instruments, e.g., first and second needles 154, 156, inserted through the first and second bores 150, 152, respectively, can be parallel to one another and have longitudinal axes aligned with the bores' axes 150A, 152A that intersect the guide rod opening 118. Regardless of the location of the guide block 108 along the first arc 106, the second arc 110 can be configured such that when it is mated to the guide block 108, the second arc's bores 150, 152 can be coaxial with the guide block's bores 130, 132, e.g., the second arc's bores' first and second longitudinal axes 150A, 152A can be the same as the guide block's first and second longitudinal axes 130A, 132A. The second arc's bores' first and second longitudinal axes 150A, 152A can therefore also pass through the guide rod opening 118 when the second arc 110 is mated to the guide block 108.

Figure 19:
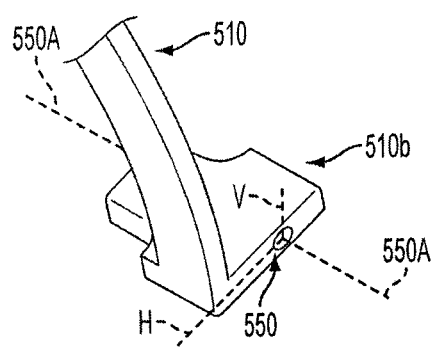
FIG. 19 is a perspective view of another embodiment of an end of a medial-lateral arc having a single bore formed therethrough.

In another embodiment illustrated in FIG. 19, a medial-lateral or second arc 510 can include a second end 510b having only one bore 550 formed therethrough. As in the illustrated embodiment, the single bore 550 can be a central bore centered in the second arc's second end horizontally H and vertically V. Similar to the embodiment of FIGS. 1 and 16, when a first end (not shown) of the second arc 510 is detachably mated to a guide block (not shown), regardless of a location of the guide block along a first arc of a frame (not shown), the second arc 510 can be configured such that a longitudinal axis 550A of the sole bore 550 can pass through a distal opening (not shown) of a guide rod of the frame. The sole bore's longitudinal axis 550A can be aligned relative to longitudinal axes of first and second bores formed through the guide block such that the sole bore's longitudinal axis 550A can be parallel to the longitudinal axes of first and second bores and be positioned therebetween.

As mentioned above, each of the bores 150, 152 of the FIGS. 1, 14, and 18 embodiment, as well as the bore 550 of the FIG. 19 embodiment, can be configured to have an instrument such as a needle advanced therethrough, e.g., the needles 154, 156. The needles 154, 156 can have a variety of configurations. In an exemplary embodiment, the needles 154, 156 can each be substantially rigid members and each include an elongate shaft 154s, 156s extending distally from a proximal collar 154c, 156c. Each of the elongate shafts 154s, 156s can include a depth indicator 154i, 156i in proximal portions thereof. The depth indicators 154i, 156i can have a variety of configurations, such as one or more marks on each of the shafts 154s, 156s. The marks can be visual marks, e.g., lines, colors, lights, etc., and/or tactile marks, e.g., grooves, etc. Generally, because a distance between the ends 110a, 110b of the second arc 110 is fixed, because longitudinal lengths of the needles 154, 156 are fixed, and because longitudinal lengths of the drills 134, 136 respectively inserted through the guide block's bores 130, 132 are known and can be inserted to a predetermined position, e.g., by inserting the drills 134, 136 through the bores 130, 132 until the proximal collar portions 142, 144 abut the guide block 108, the depth indicators 154i, 156i can be positioned along their respective needles' longi-tudinal lengths so as to indicate how far into the knee bone the drills 134, 136 would penetrate therein with the guide block 108 at its current position along the first arc 106. In other words, the depth indicators 154i, 156i can be configured to help the drills 134, 136, and subsequently, cross pins, be inserted into the medial side of the knee bone and have distal ends thereof be positioned therein, e.g., without passing out of the knee bone's lateral surface and with sufficient bone stock toward a lateral side of the knee bone to allow for mechanical fixation of cross pins therein. The location of the depth indicators 154i, 156i along longitudinal lengths of their respective needles 154, 156 can be the same for each of the depth indicators 154i, 156i, e.g., each positioned at a one-quarter mark such that 25% of the needle's longitudinal length is on one side of the depth indicator and 75% of the needle's longitudinal length is on the other side of the depth indicator.

The needles' elongate shafts 154s, 156s can have diameters smaller than diameters of the bores 150, 152, while the proximal collars 154c, 156c can have diameters, at least at distal ends thereof, that are greater than the diameters of the bores 150, 152. In this way, the proximal collars 154c, 156c can be configured as stops to prevent the needles 154, 156 from being inserted too far into the bores 150, 152 and becoming difficult to handle. Respective distal tips 154t, 156t of the needles 154, 156 can be pointed, sharp, and/or otherwise configured to penetrate through tissue.

In use, as mentioned above, the cross-pinning guide devices disclosed herein can be used in a minimally invasive surgical procedure for cross-penning a ligament graft in a bone tunnel. Generally, the patient can first be prepared for the surgery using standard techniques. An anterolateral (AL) arthroscopic viewing portal can be created in the patient's knee, as well as an anteromedial (AM) working portal. These standard surgical portals are not illustrated in the Figures. Also not shown in the Figures are skin incision(s) that can be used in performing various aspects of the procedure. A suitable graft can be provided, for example, through harvesting a semitendinosus graft from the patient, or by providing an allograft, although any type and source of graft can be implanted using the methods of this invention, including soft tissue grafts and grafts terminated with bone blocks or substitute rigid materials.

Figure 20:
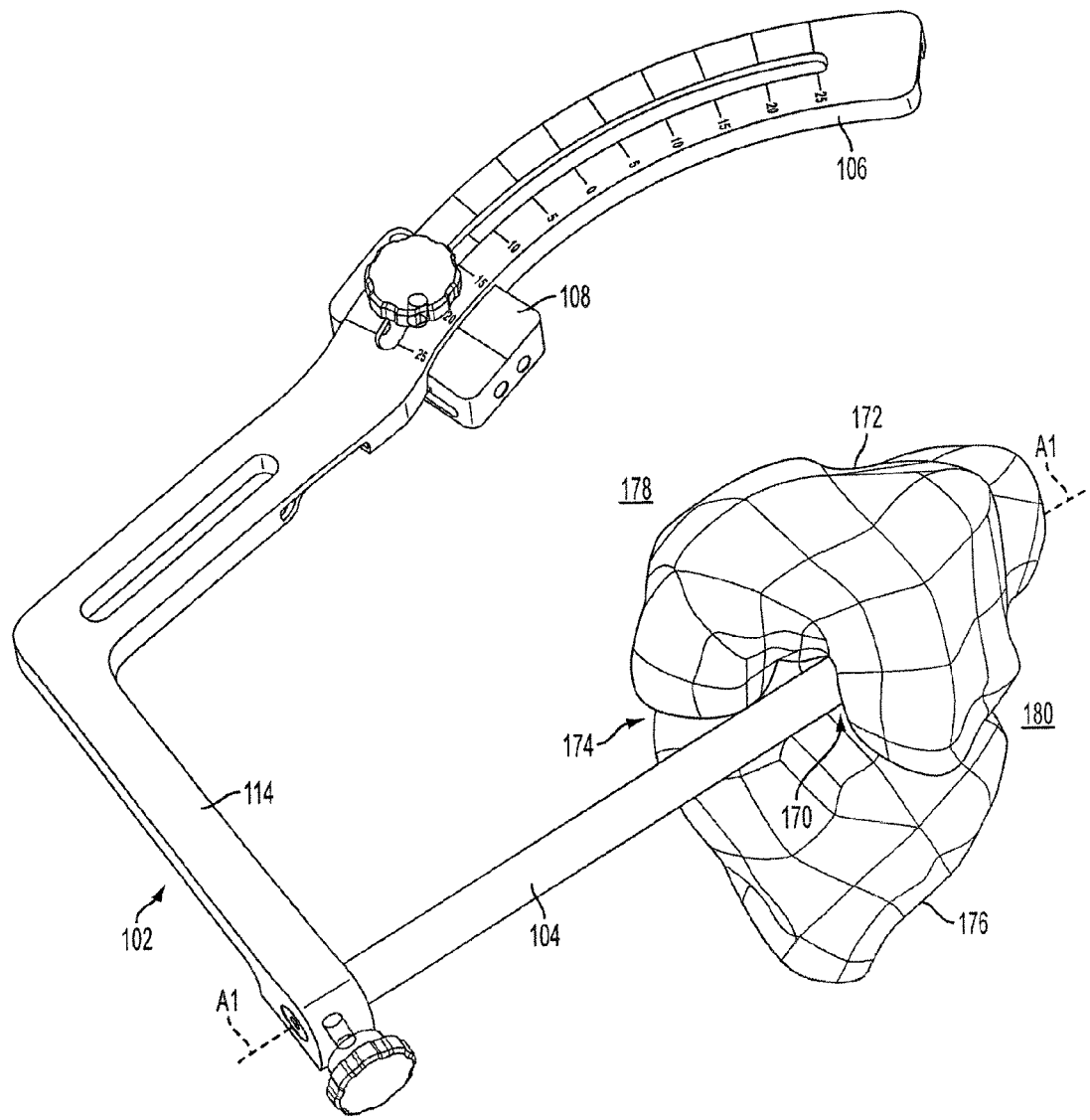
FIG. 20 is a perspective view of a guide rod of the frame of FIG. 1 inserted into a bone tunnel formed in a femur.

In an exemplary embodiment illustrated in FIG. 20, a cross pinning surgical procedure can include preparing a bone tunnel 170, also referred to herein as a "femoral tunnel," in a femur 172 of a knee of a patient using an anteromedial approach through a joint space 174 between the femur 172 and a tibia 176 and into the femur 172. The femoral tunnel 170 can be prepared in a variety of ways, as will be appreciated by a person skilled in the art. For non-limiting example, the femoral tunnel 170 can be formed by determining a position in the femoral notch that is appropriate for the insertion of the graft and drilling a guide pin (not shown) into the femur 172 along a selected femoral tunnel axis, followed by reaming to create the femoral tunnel 170 along the guide pin to an appropriate depth and diameter for receiving the graft. Although the femoral tunnel can have two open ends, the femoral tunnel 170 can, as in this illustrated embodiment, have only one open end, e.g., be a blind tunnel. Although a femoral tunnel is formed in this illustrated embodiment, as mentioned above, a cross pinning surgical procedure can instead include forming a tibial tunnel.

A guide rod, e.g., the guide rod 104 of the device 100 of FIG. 1, can be inserted into the femoral tunnel 170. In an exemplary embodiment, the guide rod 104 is attached to the base portion 114 when the guide rod 104 is inserted into the femoral tunnel 170, but the guide rod 104 can be mated to the base portion 114 after the guide rod 104 has been inserted into the femoral tunnel 170. The device of FIG. 1 is used as a non-limiting example in this illustrated embodiment. A different guide rod, e.g., a guide rod having a different diameter and/or longitudinal length than the guide rod 104, can be coupled to the base portion 114 could instead be inserted into the femoral tunnel 170, or a different cross-pinning guide device as discussed herein could be used in the procedure.

With the guide rod 104 inserted into the femoral tunnel 170, the frame 102 can be positioned on a medial side 178 of the femur 172 with the first arc 106 being positioned on the medial side 178, as illustrated in FIG. 20. In one embodiment, with the guide rod 104 inserted in the femoral tunnel 170 and with the guide rod 104 mated to base portion 114 of the frame 102, the frame 102 can be rotated about a longitudinal axis A1 of the guide rod 104 and the femoral tunnel to position the first arc 106 on the medial side 178 of the femur 172. In another embodiment, the guide rod 104 can be inserted into the femoral tunnel 170 before being mated to the base portion 114. Then, with the guide rod 104 extending from the femoral tunnel 170, the base portion 114 can be mated to the guide rod 104 so as to positioned the first arc 106 on the medial side 178. Although the frame 102 is shown in FIG. 20 without the second arc 110 mated thereto, the second arc 110 can be mated to the guide block 108 at any time during the surgical procedure. In an exemplary embodiment, the second arc 110 can be mated to the guide block 108 after the first arc 106 having the guide block 108 mated thereto is positioned on the medial side 178. If the guide block 108 is configured to be detachable from the frame 102, the guide block 108 can be attached to the frame 102, e.g., to the first arc 106, at any time during the procedure. In an exemplary embodiment, the guide block 108 can be mated to the first arc 106 prior to the first arc 106 being positioned on the medial side 178 of the femur 172.

Figure 21:
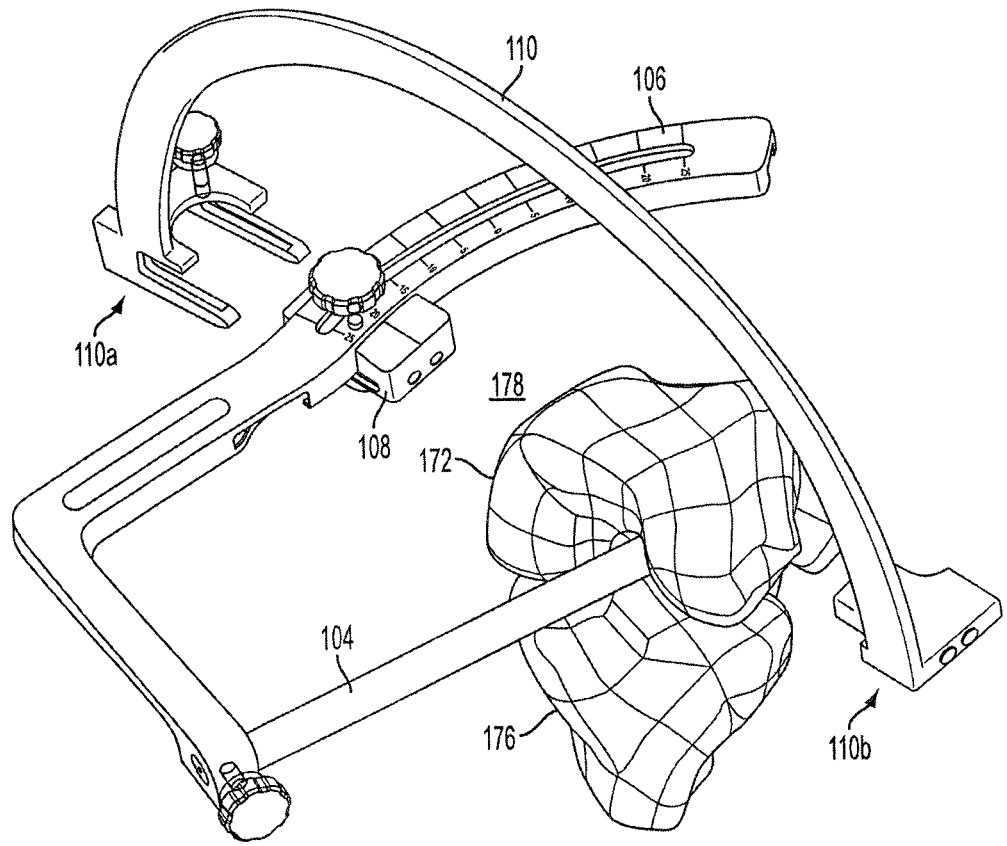
FIG. 21 is a perspective view of the guide rod of FIG. 20 inserted into the bone tunnel and of the medial-lateral arc of FIG. 1, the medial-lateral arc not being mated to the guide block and not having needles inserted therethrough.
Figure 22:
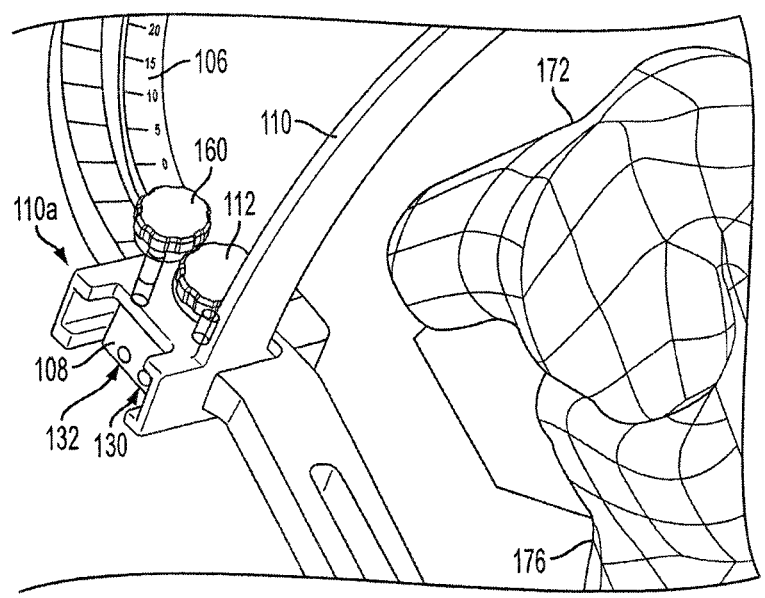
FIG. 22 is a perspective view of another end of the medial-lateral arc of FIG. 21 mated to the guide block, which is mated to the frame.
Figure 23:
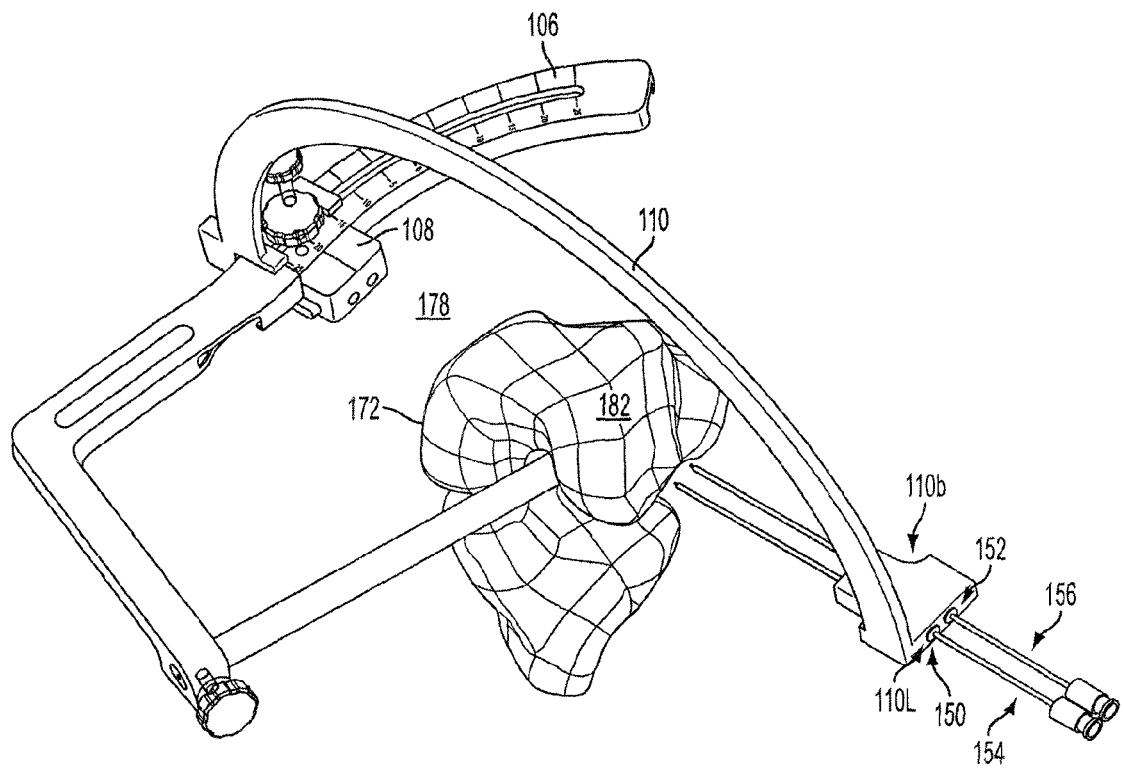
FIG. 23 is a perspective view of the medial lateral arc, the guide block, and the frame of FIG. 22 with the needles of FIG. 1 inserted through the end of the medial-lateral arc.

FIG. 21 illustrates the first arc 106 on the medial side 178 of the femur 172 and the second arc 110 in a pre-attached position extending in a medial-lateral direction. The first end 110a of the second arc 110 can be attached to the guide block 108 as discussed above, e.g., by slidably engaging the four tracks 158a, 158b, 158c, 158d with the guide block 108. Once engaged with the guide block 108, the second arc 110 can be locked in a fixed position relative thereto, as discussed above. FIGS. 22 and 23 show the second arc's first end 110a slidably engaged with the guide block 108 and the third thumbscrew 160 advanced into the corresponding bore 162 formed in the guide block 108 to lock the second arc 110 in a fixed position relative to the guide block 108. Consequently, the second arc 110 can be locked relative to the frame 102 when the guide block 108 is locked thereto via the first thumbscrew 112. FIGS. 22 and 23 show that, as mentioned above, the second arc 110 can be configured to not obstruct or otherwise prevent access to the guide block's bores 130, 132 when the second arc 110 is mated to the guide block 108.

With the first arc 106 having the guide block 108 mated thereto positioned on the medial side 178 of the femur 172, the guide block 108 can be slid along the first arc 106 to position the guide block 108 at a selected angular position therealong to position the guide block 108 relative to the femur 172, and/or the frame 102 can be rotated about the guide rod and tunnel's axis A1, to position the guide block 108 relative to the femur 172. In this way, the trajectory of the bores 130, 132 in the guide block 108 can be angularly adjusted relative to the femur 172 and to the bone tunnel 170. As discussed herein, the selected angular position can be based on the insertion depth of the needles 154, 156 inserted through the second end's bores 150, 152 and into tissue on the lateral side 180 of the femur 172. Generally, because of the general shape of femurs and because of the angle needed for an anteromedial approach into the femur 172 to intersect the bone tunnel 170, insufficient bone stock can exist on a lateral side of the bone tunnel 170, e.g., between the bone tunnel 170 and the femur's lateral surface 182. Such insufficient bone stock can hinder and/or prevent mechanical fixation of cross pins in the femur 172. Adjusting the trajectory of the bores 130, 132 based on the needles' insertion depths through the second arc 110 allows for sufficient bone stock on the lateral side of the bone tunnel 170.

If the guide block 108 is in a locked configuration, e.g., if the first thumbscrew is in the screwed configuration, the first thumbscrew 112 can be moved from the screwed configuration to the unscrewed configuration to allow the guide block 108 to slide along the first arc 106. When the guide block 108 is at the selected angular position, e.g., at the 20 degree mark as shown in FIG. 20, the guide block 108 can be locked at that position, such as by the moving the first thumbscrew 112 from the unscrewed configuration to the screwed configuration.

With the second arc 110 mated to the guide block 108, with the guide block 108 and the second arc's first end 110a positioned on the medial side 178 of the femur, and with the second arc's second end 110b positioned on a lateral side 180 of the femur, as shown in FIG. 23, the first and second needles 154, 156 can be inserted through the first and second bores 150, 152, respectively, formed in the second arc 110. The first and second needles 154, 156 can be advanced through the first and second bores 150, 152, respectively, and through tissue near the femur 172 until their respective distal tips 154t, 156t each contact the lateral surface 182 of the femur 182. The contact of the distal tips 154t, 156t with the femur's lateral surface 182 can be detected by feel and/or by vision, such as with an endoscope or other viewing instrument advanced into the patient. In an exemplary embodiment, the distal tips 154t, 156t extend through the tissue and do not form holes in or otherwise enter the femur 172 through the lateral surface 182, although the distal tips 154t, 156t may negligibly penetrate into the femur's lateral surface 182. Although both needles 154, 156 are shown in FIG. 23 as being inserted through the second arc's second end 110b prior to either of the distal tip 154t, 156t being advanced to contact the lateral surface 182 of the femur 172, the needles 154, 156 can be inserted through the second arc's bores 150, 152 simultaneously or in any order sequentially. Although using needles 154, 156 inserted through both of the second end's bores 150, 152 can help ensure that trajectories of both the guide block's bores 130, 132 are desirably positioned, in some embodiments, only one of the needles 154, 156 can be used to check the guide block's positioning, such as if the patient's femur appears to be substantially uniformly sized.

Figure 24:
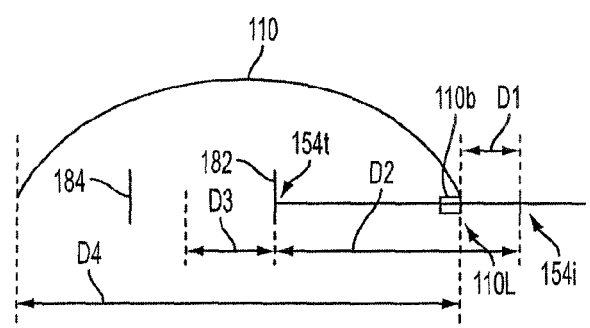
FIG. 24 is a schematic view of one of the needles of FIG. 23 inserted through the medial-lateral arc and inserted through tissue of a patient to abut a lateral surface of the femur.

With the needles' distal tips 154t, 156t contacting the femur's lateral surface 182, the needles' depth indicators 154i, 156i can indicate distances between the lateral surface 182 of the femur 172 and a target location of a distal end of a cross pin to be implanted within the femur 172, e.g., a location of the guide rod opening 118 positioned within the femoral tunnel 170. In a first case, if all of the depth indicators 154i, 156i are positioned lateral to a lateral face 110L of the second arc's second end 110b, e.g., a lateral opening of the bores 150, 152, then cross pins inserted through each of the guide block's bores 130, 132 can be inserted into the medial side 178 of the femur 172 and intersect the femoral tunnel 170 without passing through the femur's lateral surface 182, e.g., they can be contained within the femur 172. Using the first needle 154 as an example, with reference to FIG. 24, the first needle 154 can be advanced through the second arc's first bore 150 until its distal tip 154*t* contacts the femur's lateral surface 182. The depth indicator 154*i* is located a distance D1 laterally from the second end's lateral face 110L and a distance D2 laterally from the femur's lateral surface 182. The distance D1 represents a distance that is equal to or less than a distance D3 between the femur's lateral surface 182 and a lateral terminal end of a medial-lateral bone tunnel to be formed in the femur 172. In this way, the distance D1 indicates that a distance D3 exists, indicating that the bone to be drilled into the femur's medial surface will not protrude from the femur's lateral surface 182. In other words, because a distance D4 between the first and second ends 110*a*, 110*b* of the second arc is fixed, because the distance D2 between the needle's distal tip 154*t* and depth indicator 154*i* is fixed, and because the guide block's bores 130, 132 are coaxial with the second end's bores 150, 152, the depth indicator 154*i* being located lateral to the second end's lateral face 110L will indicate that a cross pin inserted through the corresponding one of the guide block's bores 130 and inserted into the medial side 178 of the femur 172 would intersect the femoral tunnel 170 without passing through the femur's lateral surface 182. The guide block 108 can therefore be presumed to be in an acceptable position for insertion of cross pins through each of the guide block's bores 130, 132.

The depth indicators 154*i*, 156*i* on the needles 154, 156 can be located thereon with a built-in safety distance such that if the depth indicators 154*i*, 156*i* are flush with the second end's lateral face 110L, the distal tips 154*t*, 156*t* thereof will be a predetermined distance, e.g., the safety distance, medial to the femur's lateral surface 182. The safety distance can vary, such as being equal to about 2 mm or being equal to about 4 mm.

Figure 25:
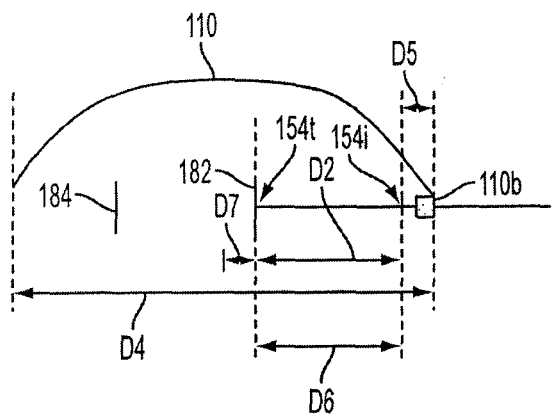
FIG. 25 is another schematic view of one of the needles of FIG. 23 inserted through the medial-lateral arc and inserted into tissue of a patient to abut a lateral surface of the femur.

Conversely, in a second case, if one or both of the depth indicators 154*i*, 156*i* are positioned medial to the lateral face 110L of the second arc's second end 110*b*, then cross pins inserted through the corresponding one or both of the guide block's bores 130, 132 and inserted into the medial side 178 of the femur 172 would pass through the femur's lateral surface 182 (or would be within the safety distance of the lateral surface 182). Such medial position(s) of the depth indicator(s) can indicate that the bores 130, 132 of the guide block 108 should be repositioned before inserting cross pins therethrough and into the femur 172. Again using the first needle 154 as an example, with reference to FIG. 25, the first needle 154 can be advanced through the second arc's first bore 150 until its distal tip 154*t* contacts the femur's lateral surface 182. The depth indicator 154*i* is located a negative distance D5, e.g., medially, since it is positioned from the second end's lateral face 110L and a distance D6 laterally from the femur's lateral surface 182. The depth indicator 154*i* may not be visible, e.g., it may be disposed within the bore 150 in the second end 110*b* or it may be disposed within tissue. The negative distance D5 is greater than a distance D7 between the femur's lateral surface 182 and the lateral terminal end of a medial-lateral bone tunnel that can be formed in the femur 172, as discussed below. In this way, because the distance D4 between the first and second ends 110*a*, 110*b* of the second arc is fixed, because the distance D2 between the needle's distal tip 154*t* and depth indicator 154*i* is fixed, and because the guide block's bores 130, 132 are coaxial with the second end's bores 150, 152, the depth indicator 154*i* being located medial to the second end's lateral face 1101, can indicate that a cross pin inserted through the corresponding one of the guide block's bores 130 and inserted into the medial side 178 of the femur 172 would intersect the femoral tunnel 170 and pass through the femur's lateral surface 182. The guide block 108 can therefore presumed to be in an unacceptable position for insertion of cross pins through each of the guide block's bores 130, 132, any of the needles 154, 156 inserted into the patient can be removed therefrom, and the guide block 108 can be slidably repositioned along the first arc 106. Slidably repositioning the guide block 108 also repositions the second arc's second end 110*b* mated to the guide block 108. With the guide block repositioned, the needles 154, 156 can again be inserted into the patient through the second end's bores 150, 152 to contact the femur's lateral surface 182, and the depth indicators' locations can be evaluated as being desirably medial or undesirably lateral to the second end's lateral face 110L. The guide block 108 repositioning, needle insertion, and depth indicator evaluation can be repeated as many times as necessary to achieve the first case in which cross pins can be inserted into the femur 172 without passing through the lateral side 182 thereof.

As mentioned above, the second end of the second arc can include only one bore formed therethrough, such as in the embodiment illustrated in FIG. 19. In such a case, only one needle can be inserted through the second end to determine whether cross pins inserted through the guide block's bores 130, 132 and into the femur 172 would pass through the femur's lateral surface 182. Because the one bore in the second end can be centered between the guide block's bores as discussed above, the single needle inserted through the one bore can be used to evaluate whether the guide block 108 is positioned for the first case (cross pins not passing through the femur's lateral surface 182) or the second case (cross pins passing through the femur's lateral surface 182).

In another embodiment, the needles 154, 156 can be used to indicate a distance as discussed above prior to formation of the femoral tunnel 170. In this embodiment, the femoral guide rod mated to the base portion 114 of the frame 102 can be "decapitated" such that it does not enter bone, e.g., the femur 172, but instead abuts an exterior surface of tissue, e.g., skin, near the bone. Alternatively, the guide rod mated to the base portion 114 of the frame 102 can be truncated such that it forms a partial length of the femoral tunnel 170 to eventually be formed. Using the needles 154, 156 to check distance prior to much, if any bone drilling, can help ensure that the tunnels and holes that are created are formed in desired positions without much, if any, readjustment.

Figure 26:
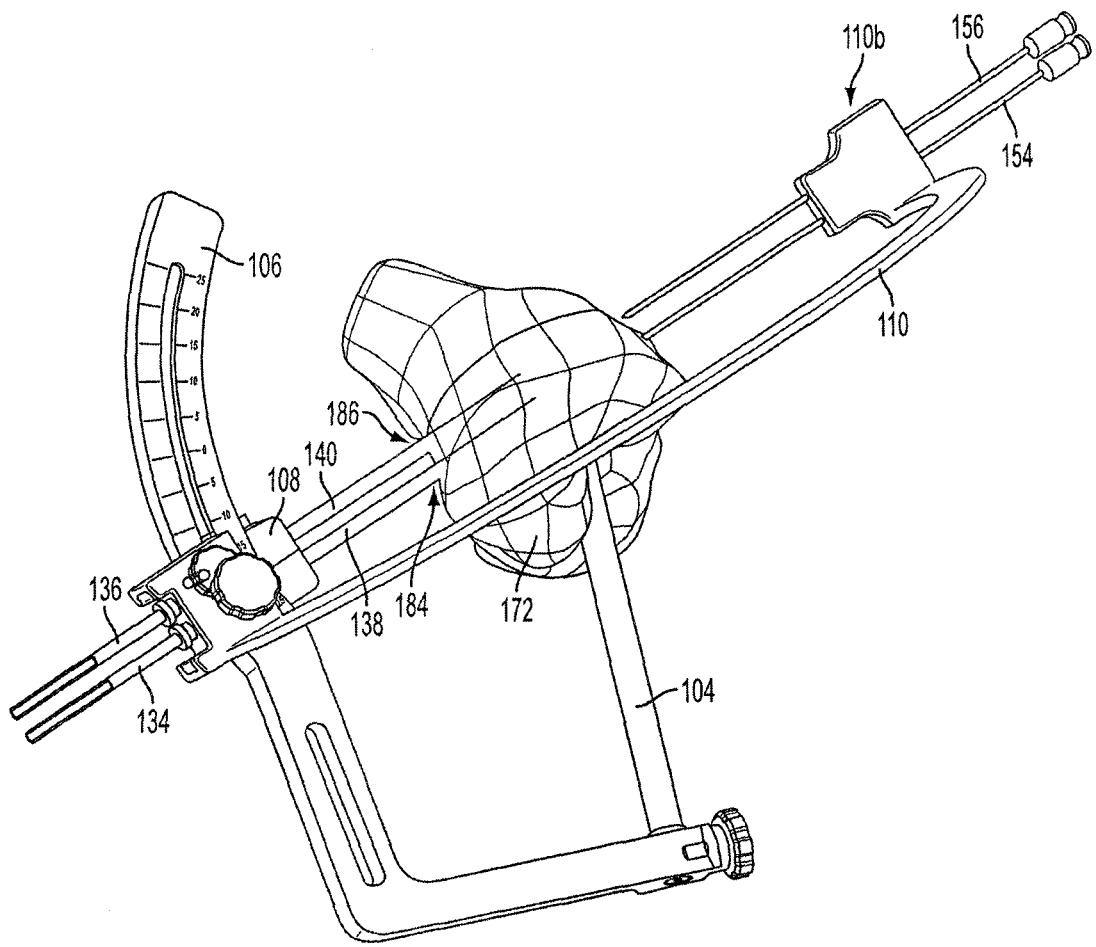
FIG. 26 is a perspective view of the medial lateral arc, the guide block, the frame, and the needles of FIG. 23 with the drills and drill sleeves of FIGS. 4 and 5 inserted through the guide block and into the femur.

With the guide block 108 at a selected position along the first arc 106, e.g., after the needles 154, 156 have been used to confirm the guide block's selected position, as illustrated in FIG. 26, the first and second drills 134, 136 and the first and second drill sleeves 138, 140 can be advanced through their respective guide block bores 130, 132 and into the medial side 178 of the femur 172 to form first and second medial-lateral pilot holes 184, 186 in the femur 172. As discussed above, the pilot holes 184, 186 can be formed so as to be substantially perpendicular to and intersect the femoral tunnel 170, e.g., at the distal opening 118 of the guide rod 104. The pilot holes 184, 186 can be formed simultaneously, or they can be formed sequentially in any order. Although the needles 154, 156 are shown in FIG. 26 as being inserted through the second end's bores 150, 152 when the first and second drills 134, 136 and the first and second drill sleeves 138, 140 can be advanced through their respective guide block bores 130, 132, the needles 154, 156 can be removed therefrom prior to using the drills 134, 136 and/or drill sleeves 138, 140. After formation of the pilot holes 184, 186, at least the drills 134, 136 can be removed therefrom to prepare for insertion of cross pins.

A ligament graft (not shown) can be inserted and positioned in the femoral tunnel 170. The graft can be inserted therein in a variety of ways. Methods for preparing a graft for implantation and for positioning a graft in a bone bore are well known in this art. For non-limiting example, the graft can be positioned in the femoral tunnel 170 by using a passing pin (not shown) placed through a guide hole (not shown) formed during the preparation of the femoral tunnel 170, to pull the graft into the femoral tunnel 170 via a suture attached between the graft and the passing pin.

With the graft positioned in the femoral tunnel 170, the cross pins, e.g., like the cross pin 146, can be medially inserted through the pilot holes 184, 186, e.g., using the insertion tool 148, to engage and pin the graft within the femoral tunnel 170. The cross pins can be inserted simultaneously, or they can be inserted sequentially in any order. In an embodiment where a graft terminates in a bone block, e.g., for implanting a bone-tendon-bone (BTB) graft, an additional drilling step can be performed after the graft has been placed in the femoral tunnel 170. This additional drilling step can be performed by, for non-limiting example, passing a stepped-diameter trocar through the respective trocar sleeve positioned in bone for receiving a cross-pin, and through the graft, before inserting the cross-pin.

Figure 27:
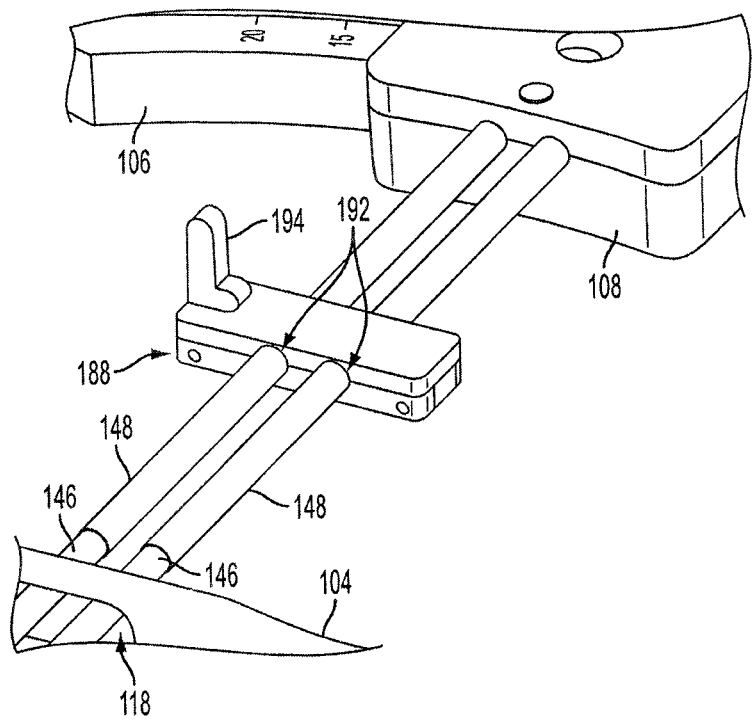
FIG. 27 is a perspective view of a depth indicator in a clamped configuration mated to the insertion tools of FIG. 13 inserted through the guide block of FIG. 1.

Inserting the cross pins can include imparting an axial, laterally-directed force to penetrate the cross pins through the graft and securely pin the graft, such as by malleting a proximal end of the insertion tool 148. A depth inserter can be configured to prevent this axial force from advancing the cross pins too far laterally, e.g., through the femur's lateral surface 182. FIG. 27 illustrates one embodiment of a depth inserter 188. For clarity of illustration, the femur 172 and graft are not shown in FIG. 27. The depth inserter 188 can include at least one bore formed therethrough, e.g., first and second bores 190, 192. The illustrated bores 190, 192 are cylindrical, but the bores 190, 192 can have any shape. The depth inserter 188 can be configured to be movable between an unclamped position, in which the bores 190, 192 each have a first diameter, and a clamped position, in which the bores 190, 192 each have a second, smaller diameter. In this way, instruments inserted through the bores 190, 192 can be preventing from moving, e.g., be locked, therein when the depth inserter 188 is in the clamped configuration, thereby holding or gripping the instruments in a fixed position. The depth inserter 188 can be configured to move between the clamped and unclamped configurations in a variety of ways, such as by actuating an actuator, e.g., a depressible button, a lever, etc., coupled to the depth inserter 188. The actuator in the illustrated embodiment includes a movable lever 194, which is shown in FIG. 27 in a position corresponding to the depth inserter 188 being in the clamped configuration. The depth inserter 188 can be formed in any way and of any one or more materials, such as a biocompatible metal molded into shape.

As illustrated in FIG. 27, the depth inserter 188 can be positioned external to the patient between the guide block 108 and the medial side 178 of the femur 172. The depth inserter 188 can be positioned to abut the medial side 178 of the femur 172, e.g., a medial surface (not shown) of tissue near the femur 172). In an exemplary embodiment, prior to clamping the depth inserter 188 around the insertion tools 148, the insertion tools 148 with the cross pins 146 at distal ends thereof can be inserted into the patient at any depth, such as to position the cross pins 146 near the graft positioned in the opening 118 of the guide rod 104, which in FIG. 27, as mentioned above, does not show the graft positioned therein. Then, the depth inserter 188 can be clamped around the insertion tools 148 to prevent axial movement thereof when the cross pins 146 are inserted through the graft. The depth inserter 188 can be unclamped from the insertion tools 148 prior to removing the insertion tools 148 from the patient, although if a distance between the depth inserter 188 and the guide block 108 is of adequate size, the insertion tools 148 may be able to be moved in a medial direction and out of the patient with the depth inserter 188 clamped therearound.

The depth inserter 188 can additionally or alternatively be used when drilling the pilot holes 184, 186.

With the graft pinned in the femoral tunnel 170, the guide rod 104 and any instruments inserted through any of the bores 130, 132, 150, 152 and remaining in the patient, e.g., the insertion tool 148, the needles 154, 156, etc., can be removed from the patient, leaving the cross pins and graft disposed in the patient. As mentioned above, in an exemplary embodiment, the cross pins can be bio-absorbable such that they do not need to be surgically removed from the patient.

Optionally, before the femoral tunnel 170 is drilled, a placement guide can be used to help determine a placement of the femoral tunnel 170 and the medial-lateral pilot holes 184, 186 before formation of one or more of the femoral tunnel 170 and the medial-lateral pilot holes 184, 186. Generally, the placement guide can be configured to mate to the frame 102 and to help ensure that if the femoral tunnel 170 is drilled at a particular location in the femur 172 that the femur 172 has sufficient bone stock to allow for the femoral tunnel 170 and the medial-lateral pilot holes 184, 186 to be formed in the femur 172. In this way, sufficiency of bone stock can be confirmed before any instruments are drilled into the femur 172 to form the femoral tunnel 170 and/or before any instruments penetrate into skin around the femur 172. Such confirmation can reduce chances of a femoral tunnel needing to be redrilled at another location where sufficient bone stock exists, thereby improving safety, saving time, and/or and reducing chances of patient injury.

Figure 28:
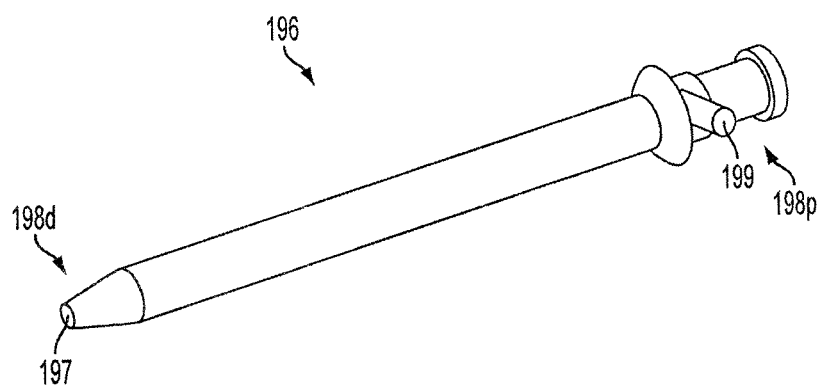
FIG. 28 is a perspective view of an embodiment of a placement guide.

FIG. 28 illustrates an exemplary embodiment of a placement guide 196. As in the illustrated embodiment, the placement guide 196 can include a substantially cylindrical cannulated shaft having an inner lumen 197 extending along its longitudinal length between proximal and distal ends 198p, 198d thereof. Cannulation of the placement guide 196 can allow for an instrument e.g., a guide wire, a drill pin, etc., to be inserted through the placement guide 196, as discussed further below. Although the distal end 198d of the placement guide 196 is tapered in a truncated cone shape in the illustrated embodiment, the distal end 198d can have a variety of shapes, e.g., conical, flat or planar, beveled, etc. The tapered distal end 198d can aid in visualizing where an instrument advanced distally through the inner lumen 197 will exit the inner lumen 197.

Figure 29:
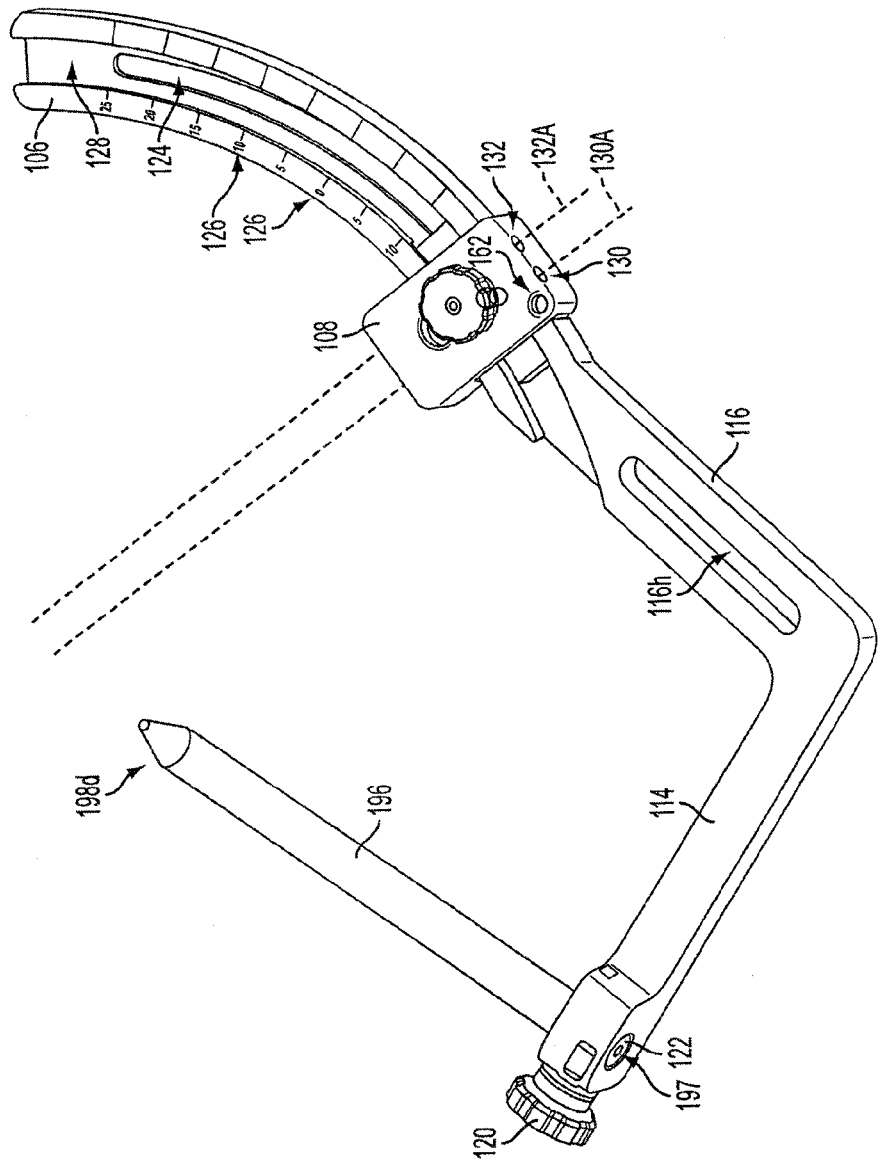
FIG. 29 is a perspective view of the placement guide of FIG. 28 mated to the frame of FIG. 1.

The placement guide 196 can be configured to mate to the base portion 114 of the frame 102 such that, as shown in FIG. 29, the placement guide's distal end 198d is spaced a distance away from the base portion 114 along a longitudinal length of the placement guide 196, the placement guide 196 is spaced a distance apart from the arm portion 116 of the frame 102, and the first arc 106 extends in a direction substantially parallel to a direction of the placement guide 196. In an exemplary embodiment, the placement guide 196 can be configured to mate to the base portion 114 at a same location as the guide rod 104 such that the placement guide 196 and the guide rod 104 can be selectively and interchangeably mated to the base portion 114. The placement guide 196 can be configured to detachably mate to the base portion 114 of the frame 102 by mating the proximal end 198p of the placement guide 196 to the end of the base portion 114, e.g., by inserting the proximal end 198p of the placement guide 196 into the hole 122 formed in the base portion 114. The placement guide 196 can be configured to be locked in a mated position relative to the base portion 114, e.g., by snap fit as with a protrusion 199 as in the illustrated embodiment, matable threads, the second thumbscrew 120 as in the illustrated embodiment, etc. Providing a detachable placement guide can facilitate cleaning of the placement guide 196 and the frame 102 as well as allow the frame 102 to be used in planning placement of the femoral tunnel 170 as well as in forming the femoral tunnel 170. The frame 102 can be provided as part of a kit including the detachable placement guide 196 as one of a plurality of placement guides each configured to detachably mate to the frame 102. Such a kit can also include one or more guide rods, as discussed above. The plurality of placement guides can have a variety of longitudinal lengths and diameters to accommodate various graft sizes and patient anatomies.

The placement guide 196 can be configured to be used in connection with formation of femoral bone tunnels and tibial bone tunnels. For use in connection with formation of a tibial bone tunnel, the placement guide 196 can be configured to mate to a base portion of a frame via an adaptor, similar to that discussed above regarding the guide rod 204 of FIGS. 3 and 4. The same adaptor can be configured to mate a guide rod and a placement guide to a base portion of a frame.

The longitudinal length of the placement guide 196 can be less than a longitudinal length of the guide rod 104 such that when the guide rod 104 is mated to the base portion 114, the guide rod 104 extends a greater distance away from the base portion 114 than when the placement guide 196 is mated to the base portion 114. In other words, when the guide rod 104 is mated to the base portion 114, the first and second longitudinal axis 130A, 132A can pass through the opening 118 of the guide rod 104, as illustrated in FIG. 2. In contrast, when the placement guide 196 is mated to the base portion 114, as illustrated in FIG. 29, the first and second longitudinal axis 130A, 132A can be located distal to the placement guide's distal end 198d such that the first and second longitudinal axis 130A, 132A do not intersect the placement guide 196. The placement guide 196 can be shorter than the guide rod 104 by any amount, e.g., 30 mm. By having a shorter longitudinal length than the guide rod 104, the placement guide 196 can be configured to not penetrate into the femur 172 and/or into skin around the femur 172 when positioned relative thereto, as shown in FIG. 30.

If the placement guide 196 is used in a surgical procedure, as mentioned above, it can be used before formation of the femoral tunnel 170. In other words, the placement guide 196 can be mated to the base portion 114 before the guide rod 104 is mated thereto, and the guide rod 104 can be subsequently mated to the base portion 104 after the placement guide 196 is used to help determine proper positioning of the femoral tunnel 170 to be drilled. As shown in the embodiment of FIG. 30, with the placement guide 196 mated to the base portion 114, the placement guide 196 can be positioned relative to the femur 172 with the placement guide's distal end 198d adjacent to the femur 172. In the illustrated embodiment, the placement guide's distal end is configured to penetrate tissue and abut an outer surface of the femur 172, and any remnant ACL tissue, to help maintain positioning of the placement guide 196 relative to the femur 172. The placement guide's distal end can be configured to penetrate tissue and/or bone, such as by including a penetrating element, e.g., a coarse textured surface, one or more teeth, etc. In some embodiments, the placement guide's distal end 198d can be configured to abut tissue, e.g., skin around the femur 172, without penetrating into the tissue, e.g., the distal end 198d is a blunt end.

Figure 30:
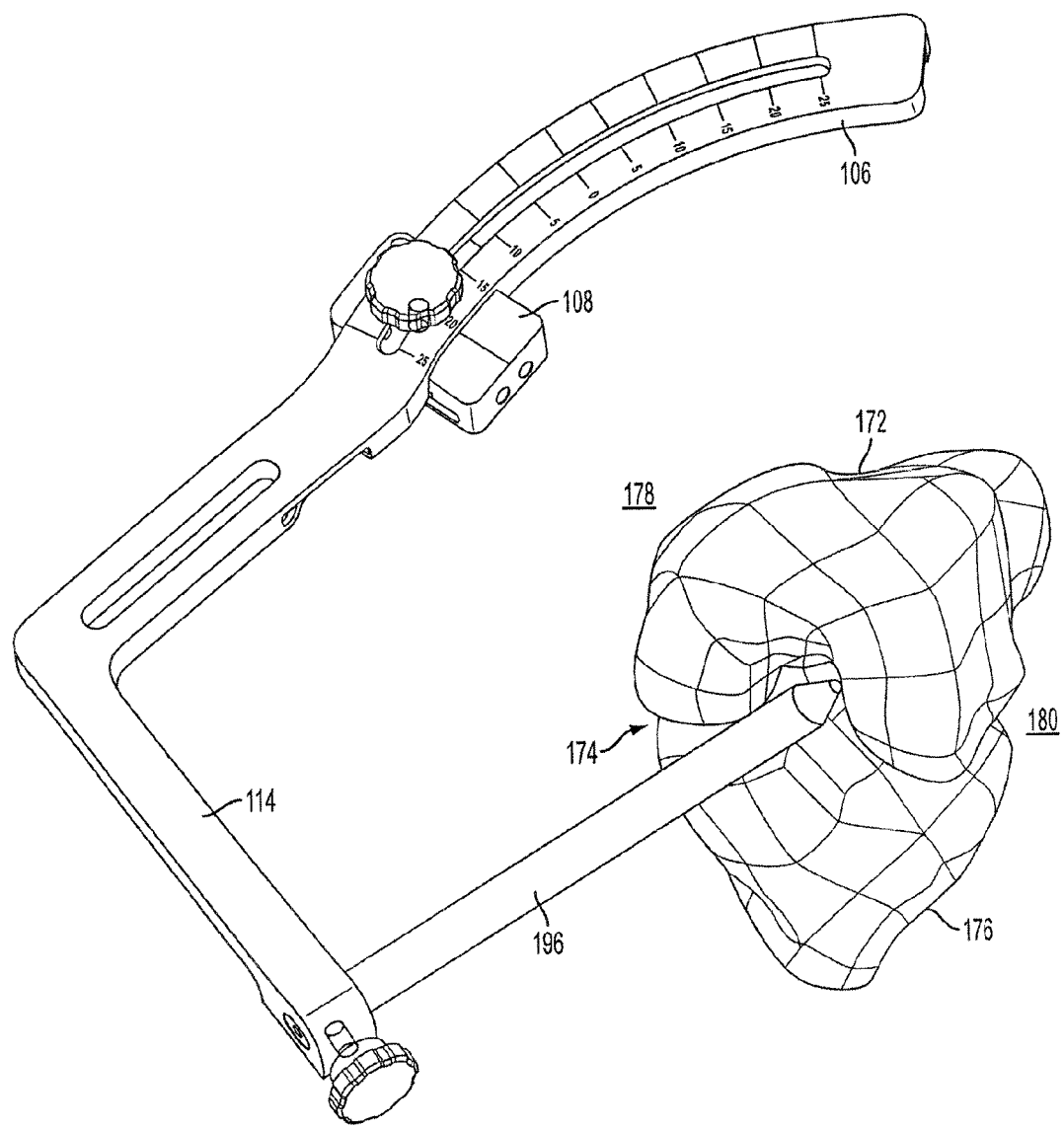
FIG. 30 is a perspective view of the placement guide and the frame of FIG. 29 positioned relative to a femur.

With the placement guide 196 positioned relative to the femur 172, the frame 102 mated to the placement guide 196 can be positioned on the medial side 178 of the femur 172 with the first arc 106 being positioned on the medial side 178, as shown in FIG. 30. Although the frame 102 is shown in FIG. 30 without the second arc 110 mated thereto, the second arc 110 can be mated to the guide block 108 at any time during the surgical procedure. In an exemplary embodiment, when using the placement guide 196, the second arc 110 can be mated to the guide block 108 after the first arc 106 having the guide block 108 mated thereto is positioned on the medial side 178. Once engaged with the guide block 108, the second arc 110 can be locked in a fixed position relative thereto and used to angularly adjust the trajectory of the bores 130, 132 in the guide block 108 relative to the femur 172, as discussed above. In this way, the trajectories of the bores 130, 132 based on the needles' insertion depths through the second arc 110 can be adjusted before the femoral tunnel 170 is formed. However, even if the placement guide 196 is used to help determine placement of the femoral tunnel 170 before the femoral tunnel 170 and is formed in the femur 172, the second arc 110 can be used again after formation of the femoral tunnel 170 as secondary verification.

In some embodiments, a pilot hole having a smaller diameter than the femoral tunnel 170 can be drilled into the femur 172 at a selected location of the femoral tunnel 170. The placement guide 196 can be used to verify that sufficient bone stock exists before the larger diameter femoral tunnel 170 is drilled at the location of the pilot hole. For non-limiting example, a pin, e.g., a drill pin, can be positioned within the pilot hole and extend out of the femur 172. The placement guide 196 can be inserted over the drill pin such that the drill pin extend through the inner lumen 197, and placement of the hole can be verified using the second arc 110 similar to that discussed above.

The various methods and devices disclosed herein can be used in a variety of surgical procedures, however the methods and devices are particularly useful for repairing an ACL in a human knee. In an ACL repair, the torn ACL can be replaced with at least one ligament graft which is anchored to a knee bone, e.g., a femur or a tibia. The term "ligament graft," as used herein, is intended to include natural materials, such as autografts, allografts, and xenografts, including harvested ligaments and tendons, as well as synthetic materials. A ligament graft can also include an anchoring element attached thereto for anchoring the graft to the knee bone. For example, the ligament graft can include a bone graft, plug, or other member, attached to one or both terminal ends thereof. The term "bone graft," as used herein, in intended to include natural materials, such as autografts, allografts, and xenografts, as well as synthetic materials. A person skilled in the art will appreciate that the various methods and devices disclosed herein can be used in a variety of surgical procedures, and that the particular configuration of the ligament grafts can vary depending on the intended use, and virtually any ligament grafts known in the art can be used with the devices and methods disclosed herein.

A person skilled in the art will appreciate that the present invention has application in conventional endoscopic and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a frame having a guide rod and a proximal-distal arc spaced a distance apart from the guide rod;
   a guide block slidably mounted on the proximal-distal arc and having at least one bore formed therethrough that is configured to receive a first surgical instrument; and
   a medial-lateral arc having a first end with an engagement mechanism configured to detachably mate the medial-lateral arc to the guide block, and a second end having one bore formed therethrough that is configured to receive a second surgical instrument;
   wherein, with the medial-lateral arc mated to the guide block, the at least one bore formed through the guide block is coaxial with the at least one bore formed through the second end of the medial-lateral arc.

2. The device of claim 1, wherein the proximal-distal arc extends in a direction substantially parallel to a direction of the guide rod.

3. The device of claim 1, wherein the engagement mechanism is matable with the guide block in a first orientation relative to the guide block and in a second orientation relative to the guide block that differs from the first orientation.

4. The device of claim 1, wherein, with the medial-lateral arc mated to the guide block, the medial-lateral arc is positioned in a plane that is substantially perpendicular to a plane containing the proximal-distal arc.

5. The device of claim 1, wherein, with the guide block at any slidable position along the proximal-distal arc, a longitudinal axis of the at least one bore formed through the guide block extends through an opening formed in a distal portion of the guide rod.

6. A surgical device, comprising:
   a frame having a guide rod and a proximal-distance arc spaced a distance apart from the guide rod;
   a guide block slidably mounted on the proximal-distal arc and having at least one bore formed therethrough that is configured to receive a first surgical instrument; and
   a medial-lateral arc having a first end with an engagement mechanism configured to detachably mate the medial-lateral arc to the guide block, and a second end having at least one bore formed therethrough that is configured to receive a second surgical instrument;
   wherein the at least one bore formed through the guide block comprises first and second bores, the at least one bore formed through the second end of the medial-lateral arc comprises third and fourth bores, and with the medial-lateral arc mated to the guide block, the first bore is coaxial with the third bore and the second bore is coaxial with the fourth bore.

7. The device of claim 6, wherein the proximal-distal arc extends in a direction substantially parallel to a direction of the guide rod.

8. The device of claim 6, wherein the engagement mechanism is matable with the guide block in a first orientation relative to the guide block and in a second orientation relative to the guide block that differs from the first orientation.

9. The device of claim 6, wherein, with the medial-lateral arc mated to the guide block, the medial-lateral arc is positioned in a plane that is substantially perpendicular to a plane containing the proximal-distal arc.

10. The device of claim 6, wherein, with the guide block at any slidable position along the proximal-distal arc, a longitudinal axis of the first bore and a longitudinal axis of the second bore extend through an opening formed in a distal portion of the guide rod.

* * * * *